(12) United States Patent
Northrup et al.

(10) Patent No.: US 7,633,606 B2
(45) Date of Patent: Dec. 15, 2009

(54) INTEGRATED AIRBORNE SUBSTANCE COLLECTION AND DETECTION SYSTEM

(75) Inventors: Allen Northrup, Orinda, CA (US); Farzad Pourahmadi, Fremont, CA (US); Bob Yuan, Belmont, CA (US); Amy J. Devitt, San Carlos, CA (US)

(73) Assignee: Microfluidic Systems, Inc., Fremont, CA (US)

( * ) Notice: Subject to any disclaimer, the term of this patent is extended or adjusted under 35 U.S.C. 154(b) by 289 days.

(21) Appl. No.: 11/509,872

(22) Filed: Aug. 24, 2006

(65) Prior Publication Data

US 2008/0048874 A1    Feb. 28, 2008

(51) Int. Cl.
G01N 21/00    (2006.01)
(52) U.S. Cl. .......................................... 356/73; 422/88
(58) Field of Classification Search ................... 356/38, 356/73
See application file for complete search history.

(56) References Cited

U.S. PATENT DOCUMENTS

| | | | |
|---|---|---|---|
| 3,985,032 A | 10/1976 | Avakian | 73/425.4 |
| 4,973,450 A | 11/1990 | Schluter | 422/101 |
| 4,999,164 A | 3/1991 | Puchinger et al. | 422/100 |
| 5,475,203 A | 12/1995 | McGaffigan | 219/548 |
| 5,681,752 A | 10/1997 | Prather | 436/173 |
| 5,812,272 A | 9/1998 | King et al. | 356/445 |
| 5,851,491 A | 12/1998 | Moulton | 422/101 |
| 5,968,731 A | 10/1999 | Layne et al. | 435/5 |
| 6,033,880 A | 3/2000 | Haff et al. | 435/91.1 |
| 6,087,183 A * | 7/2000 | Zaromb | 436/178 |
| 6,123,905 A | 9/2000 | Torti et al. | 422/100 |
| 6,134,944 A | 10/2000 | Yu et al. | 73/23.35 |
| 6,146,591 A | 11/2000 | Miller | 422/65 |
| 6,228,634 B1 | 5/2001 | Blumenfeld et al. | 435/286.1 |
| 6,318,158 B1 | 11/2001 | Breen et al. | 73/64.56 |
| 6,374,684 B1 | 4/2002 | Dority | 73/864.81 |

(Continued)

FOREIGN PATENT DOCUMENTS

WO    WO 2005/078674 A2    8/2005

OTHER PUBLICATIONS

"High Sensitivity PCR Assay in Plastic Micro Reactors", Jianing Yang et al., Physical Sciences Research Laboratories, Motorola Labs, Motorola, Inc., 7700 S. River Parkway, MD-ML34, Tempe, AZ 85284, USA, Revised Aug. 29, 2002, pp. 179-187.

(Continued)

*Primary Examiner*—Roy Punnoose
(74) *Attorney, Agent, or Firm*—Haverstock & Owens LLP

(57) ABSTRACT

A collection and detection system is configured as a detect to warn system in which the presence of specific types of particles are detected, and may or may not be identified. An air collection module intakes ambient air, detect the presence of one or more different types of airborne particles within the ambient air, and collect the airborne particles, such as within a fluid. A triggering mechanism is positioned to continuously monitor the airflow, to determine one or more characteristics of the airborne particles. If those measured characteristics match specific known characteristics, a trigger signal is generated. In response, a confirmation device performs a detection method on a fluid solution including the airflow particles to determine the presence of one or more different types of specific biological particles.

37 Claims, 14 Drawing Sheets

U.S. PATENT DOCUMENTS

| | | | |
|---|---|---|---|
| 6,391,541 B1 | 5/2002 | Petersen et al. | 435/5 |
| 6,481,290 B1 | 11/2002 | MacInnis et al. | 73/644 |
| 6,482,362 B1 | 11/2002 | Smith | 422/100 |
| 6,562,209 B1 | 5/2003 | Sullivan et al. | 204/403.01 |
| 6,565,815 B1 | 5/2003 | Chang et al. | 422/198 |
| 6,694,799 B2 | 2/2004 | Small | |
| 6,741,174 B2 * | 5/2004 | Rhoades et al. | 340/540 |
| 6,746,864 B1 | 6/2004 | McNeil et al. | 435/288.7 |
| 6,766,277 B2 | 7/2004 | Siegel | 702/187 |
| 6,770,246 B1 | 8/2004 | Husek | 422/101 |
| 6,787,104 B1 | 9/2004 | Mariella, Jr. | 422/4 |
| 6,800,452 B1 | 10/2004 | McNeil et al. | 435/29 |
| 6,905,885 B2 | 6/2005 | Colston et al. | 436/518 |
| 6,951,147 B2 | 10/2005 | Call et al. | 73/863.22 |
| 6,977,145 B2 | 12/2005 | Fouillet et al. | 435/6 |
| 6,979,543 B2 | 12/2005 | Chen et al. | 435/6 |
| 6,998,047 B1 | 2/2006 | Kopaciewicz et al. | 210/321.75 |
| 7,005,982 B1 * | 2/2006 | Frank | 340/539.26 |
| 7,006,923 B1 * | 2/2006 | Rubin | 702/19 |
| 7,070,935 B2 | 7/2006 | Schaudies et al. | 435/6 |
| 7,082,369 B1 * | 7/2006 | Rubin et al. | 702/19 |
| 7,106,442 B2 * | 9/2006 | Silcott et al. | 356/338 |
| 7,228,067 B2 | 6/2007 | Magni et al. | 392/480 |
| 7,318,911 B2 | 1/2008 | Smith | 422/100 |
| 7,470,546 B2 | 12/2008 | Lehmann | 436/180 |
| 2001/0032666 A1 | 10/2001 | Jenson et al. | 136/256 |
| 2001/0036630 A1 | 11/2001 | Ibrahim | 435/6 |
| 2002/0022261 A1 | 2/2002 | Anderson et al. | 435/287.5 |
| 2002/0039783 A1 | 4/2002 | McMillan et al. | 435/287.2 |
| 2002/0142482 A1 | 10/2002 | Wu et al. | 436/177 |
| 2003/0003441 A1 | 1/2003 | Colston et al. | 435/5 |
| 2003/0073229 A1 | 4/2003 | Greenstein et al. | 435/287.2 |
| 2003/0153021 A1 | 8/2003 | Lu et al. | 435/7.32 |
| 2004/0038385 A1 | 2/2004 | Langlois et al. | 435/287.1 |
| 2004/0142488 A1 | 7/2004 | Gierde et al. | 436/178 |
| 2004/0197793 A1 | 10/2004 | Hassibi et al. | 435/6 |
| 2004/0259234 A1 | 12/2004 | Chou et al. | 435/287.1 |
| 2005/0026276 A1 | 2/2005 | Chou | 435/287.2 |
| 2005/0056785 A1 | 3/2005 | Chou et al. | 250/338.1 |
| 2005/0064598 A1 | 3/2005 | Yuan et al. | 436/63 |
| 2005/0142565 A1 | 6/2005 | Samper et al. | 435/6 |
| 2005/0157301 A1 | 7/2005 | Chediak et al. | 356/417 |
| 2005/0190058 A1 | 9/2005 | Call | 340/539.26 |
| 2005/0227275 A1 | 10/2005 | Jung et al. | 435/6 |
| 2005/0239192 A1 | 10/2005 | Nasarabadi et al. | 435/287.1 |
| 2005/0266585 A1 | 12/2005 | Bargh | 436/177 |
| 2006/0006327 A1 | 1/2006 | Donaldson et al. | 250/288 |
| 2006/0057599 A1 | 3/2006 | Dzenitis et al. | 435/6 |
| 2006/0063160 A1 | 3/2006 | West et al. | 435/6 |
| 2006/0073484 A1 | 4/2006 | Mathies et al. | 435/6 |
| 2006/0073585 A1 | 4/2006 | McDevitt et al. | 435/288.7 |
| 2006/0079000 A1 * | 4/2006 | Floriano et al. | 436/164 |
| 2006/0197033 A1 | 9/2006 | Hairston et al. | 250/458.1 |
| 2006/0219939 A1 | 10/2006 | Satyanarayana et al. | 250/458.1 |
| 2006/0257853 A1 | 11/2006 | Herman | 435/5 |
| 2007/0116607 A1 * | 5/2007 | Wang et al. | 422/83 |
| 2008/0050803 A1 * | 2/2008 | Northrup et al. | 435/287.2 |
| 2008/0125330 A1 | 5/2008 | Cady et al. | |

OTHER PUBLICATIONS

Office Action mailed on Jul. 30, 2009, U.S. Appl. No. 11/510,073, Filing Date Aug. 24, 2006, Applicant, Allen Northrup, Examiner, Previl, Daniel, Art Unit 2612, 11 pages.

* cited by examiner

Fig. 2

```
540 ─ Intake Ambient Air ◄──────┐
         │                        │
545 ─ Measure Optical Characteristics │
         │                        │
         ▼                        │
550 ─ Compare to Known Optical Characteristics ── No ──┘
         │
         Yes
         ▼
555 ─ Generate Trigger Signal
         │
560 ─ Output Fluid Sample
         │
565 ─ Confirm Presence of Biological Particles
```

Fig. 11

```
625 → Intake Ambient Air ←──────── (B)
         ↓                            ↑
630 → Measure Optical Characteristics  |
         ↓                            |
635 → Convert Airborne Particles to Fluid Sample
         ↓                            |
      640  Compare                    |
           to Known Optical  ── No ───┤
           Characteristics            |
             ↓ Yes                    |
645 → Generate a Trigger Signal       |
         ↓                            |
650 → Meter and Distribute a First    |
      Portion of the Fluid Sample     |
         ↓                            |
      655  Determine                  |
           Presence of   ── No ───────┘
           Biological Particles
             ↓ Yes
660 → Generate a First Alarm Signal
         ↓
665 → Meter and Distribute Remaining Portion of
      Fluid Sample
         ↓
        (A)
```

Fig. 13

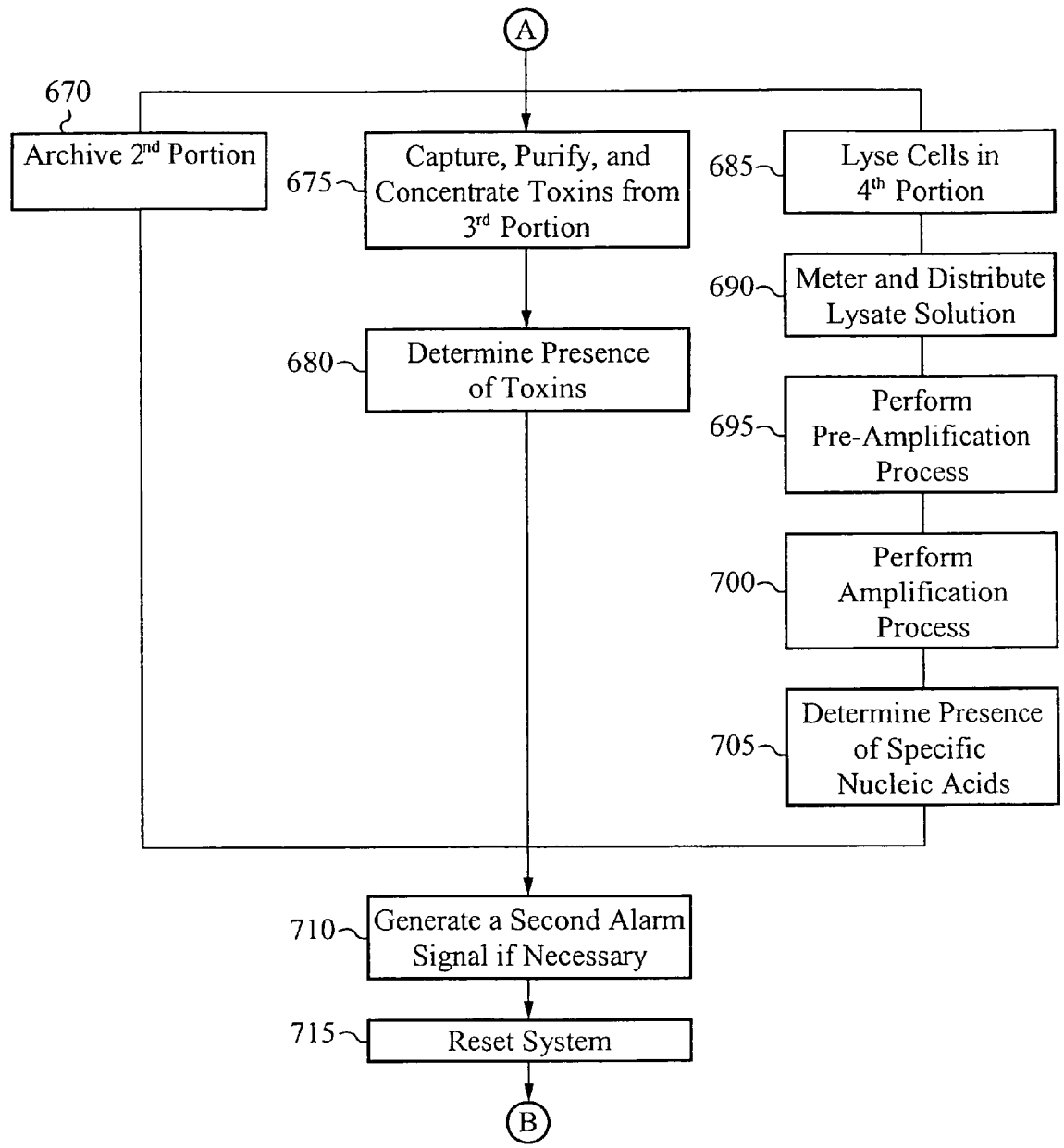
Fig. 13 (con't)

INTEGRATED AIRBORNE SUBSTANCE COLLECTION AND DETECTION SYSTEM

GOVERNMENT LICENSE RIGHT

This invention was made with Government support under Agreement No. W81XWH-04-9-0010 awarded by the Government. The Government has certain rights in this invention.

CROSS-REFERENCE TO RELATED APPLICATIONS

This patent application is related to commonly owned co-pending U.S. patent application Ser. No. 11/509,969, filed Aug. 24, 2006, entitled "An Integrated Airborne Substance Collection and Detection System", and U.S. patent application Ser. No. 11/510,073, filed Aug. 24, 2006, entitled "An Integrated Airborne Substance Collection and Detection System", which are hereby incorporated by reference in their entirety.

FIELD OF THE INVENTION

The invention relates to a method of and apparatus for collecting and analyzing particulates. More particularly, the invention relates to the collection and detection of airborne particulates.

BACKGROUND OF THE INVENTION

Bio-threat detectors are used to monitor the ambient air to detect the presence of potentially harmful pathogens. In general, air is drawn into a detection apparatus, or trigger, where the particulates in the air are evaluated. Airflow into the detection apparatus is typically generated by a fan within the apparatus. The trigger continuously monitors the air and the individual molecules within a given airflow. Some triggers use lasers to scan the air path to interrogate the particles passing through. A harmless particle, such as a dust particle, can be discriminated from a harmful particle, for example an anthrax spore, because each different type of particle reflects a different wavelength of light. The laser light reflected off the passing particles is matched to database of known harmful wavelengths. When a harmful wavelength is detected, the trigger signals that a potential pathogen is present. However, the specific type of particle is not identified by the trigger.

A confirmation process is initiated once the trigger signals the presence of a possible pathogen. During the confirmation process, the particles that triggered the detection apparatus are identified. Conventionally, when the trigger goes off, the potential pathogen is collected and taken to a lab where an analysis is performed. Multiple techniques are performed to identify the potential pathogen, each technique is designed to identify a different type of pathogen, typically performed under the supervision of a lab operator. This is a time-consuming process requiring various pieces of test equipment, which is impractical for real-time threat assessment. Such processes also require the interaction of a human operator, which is costly and often efficient. Continuous monitoring and processing of potential pathogens, that is 24 hour a day coverage, requires multiple such human operators to cover the desired time frame.

SUMMARY OF THE INVENTION

Embodiments of a collection and detection system are directed to a detect to warn system in which the presence of specific types of particles are detected, and may or may not be identified. An exemplary configuration of the integrated collection and detection system includes an air collection module, a confirmation device, and a control module.

In some embodiments, the air collection module is configured to intake ambient air, detect the presence of one or more different types of airborne particles within the ambient air, and collect the airborne particles, such as within a fluid. The air collection module includes a triggering mechanism and a fluid interface. The fluid interface is configured to receive ambient air, including airborne particles present therein, that is drawn into the collection and detection system and to collect the airborne particles into a fluid solution. The triggering mechanism is positioned to continuously monitor the airflow, and the airborne particles within the airflow, directed to the fluid interface. Through this interrogation of the ambient air, one or more optical characteristics of the airborne particles are measured.

The optical characteristics are compared to known optical characteristics to determine if one or more different types of specific biological particles are present in the airflow. If it is determined that one or more different types of specific biological particles are present, than a trigger signal is generated.

In response to the trigger signal, the confirmation device confirms the presence of the one or more different types of specific biological particles. Confirmation is performed by attempting to detect the one or more different types of biological particles within the fluid sample. In some embodiments, an immuno assay is used to detect the one or more different types of biological particles within the fluid sample.

In one aspect, a detection apparatus is configured to detect the presence of one or more different types of particles. The detection apparatus includes a first level detection device, a fluid interface, and a second level detection device. The first level detection device is configured to interrogate ambient air for the presence of one or more different types of airborne biological particles, wherein the first level detection device is further configured to generate a trigger signal in response to detecting one or more of the different types of airborne biological particles. The fluid interface is configured to receive airborne particles within the ambient air and to output a fluid sample including the particles. The second level detection device is configured to receive the fluid sample in response to the trigger signal and to confirm the presence of the one or more different types of biological particles using an immuno assay.

The detection apparatus can also include microfluidic circuitry to couple the fluid interface to the second level detection device. The microfluidic circuitry can include a collection vessel to store the fluid sample. The microfluidic circuitry can also be configured to meter the fluid sample into one or more portions and to distribute a first portion of the fluid sample to the second level detection device. The second level detection device can be configured to identify the one or more different types of biologic particles using the immuno assay. The biologic particle can be a pathogen or a toxin. The second level detection device can include one or more capture devices each configured to capture one or more different types of biological particles from the fluid sample. The second level detection device can also include an optical detection module configured to optically detect the presence of the captured one or more different types of biological particles within the one or more capture devices. The detection apparatus can also include a control module configured to control the operation of the first level detection device, the fluid interface, and the second level detection device to enable the detection apparatus to function automatically. The detection apparatus can be configured to confirm the presence of the one or more different types of biological particles within about 5 minutes from generating the trigger signal. The first level detection device can include an air collection device configured to intake the ambient air to be interrogated. The first level detection device can also include a triggering mechanism configured to monitor the ambient air taken in by the air collection device and to generate the trigger signal. The triggering mechanism can include a light source configured to direct light onto the airborne particles and a light collector configured to measure one or more optical characteristics of light impinging the airborne particles.

In another aspect, an autonomously functioning detection apparatus is configured to detect the presence of one or more different types of particles. The autonomously functioning detection apparatus includes a first level detection device, a fluid interface, a second level detection device, and a control module. The first level detection device is configured to automatically interrogate ambient air for the presence of one or more different types of airborne biological particles, wherein the first level detection device is further configured to automatically generate a trigger signal in response to detecting one or more of the different types of airborne biological particles. The fluid interface is configured to automatically receive airborne particles within the ambient air and to automatically output a fluid sample including the particles. The second level detection device is configured to automatically receive the fluid sample in response to the trigger signal and to automatically confirm the presence of the one or more different types of biological particles. The control module is configured to provide control signals to the first level detection device, the fluid interface, and the second level detection device to enable the detection apparatus to function autonomously.

In yet another aspect, a detection apparatus is configured to detect the presence of one or more different types of particles. The detection apparatus includes an air collection device, a triggering mechanism, a fluid interface, a confirmation device, and a control module. The air collection device is configured to intake ambient air including airborne particles. The triggering mechanism is configured to interrogate the ambient air for the presence of one or more different types of airborne biological particles and to generate a trigger signal in response to detecting one or more of the different types of airborne biological particles. The fluid interface is configured to receive airborne particles within the ambient air and to output a fluid sample including the particles. The confirmation device is configured to receive the fluid sample in response to the trigger signal and to confirm the presence of the one or more different types of biological particles using an immuno assay. The control module is configured to provide control signals to the air collection device, the triggering mechanism, the fluid interface, and the confirmation device to enable the detection apparatus to function autonomously.

In still yet another aspect, a method of detecting the presence of one or more different types of biological particles is described. The method includes collecting ambient air including airborne particles, measuring one or more optical characteristics of the airborne particles, comparing the measured one or more optical characteristics to known optical characteristics associated with one or more types of biological particles, generating a trigger signal if the one or more of the measured one or more optical characteristics match one or more of the known optical characteristics, converting the airborne particles to a fluid sample, and analyzing the fluid sample according to an immuno assay to confirm the presence of the one or more specific types of biological particles.

BRIEF DESCRIPTION OF THE DRAWINGS

FIG. 2 illustrates an exemplary functional block diagram of a first embodiment of the integrated collection and detection system.

FIG. 11 illustrates an exemplary automated process performed by the second embodiment of the particle collection and detection system.

FIG. 13 illustrates an exemplary automated process performed by the third embodiment of the particle collection and detection system.

Figure 1:
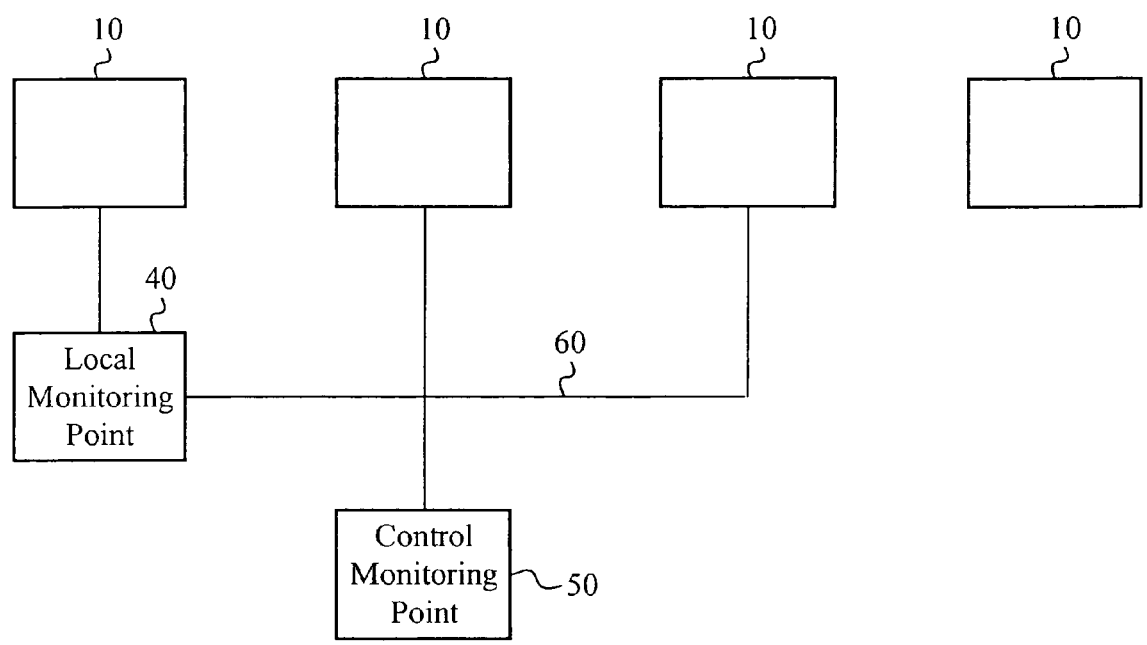
FIG. 1 illustrates an exemplary network configuration including multiple collection and detection systems.

Embodiments of the integrated particle collection and detection system are described relative to the several views of the drawings. Where appropriate and only where identical elements are disclosed and shown in more than one drawing, the same reference numeral will be used to represent such identical elements.

DETAILED DESCRIPTION OF THE PRESENT INVENTION

Embodiments of the present invention are directed to a fully integrated and autonomous, collection and detection system configured to monitor the ambient air for specific particles, such as pathogens. In some embodiments, the collection and detection system is configured as an integrated cartridge. In some embodiments, the collection and detection system is configured as a fully autonomous system. An air collector captures airborne particles and outputs a fluid sample including the captured particles in a fluid solution. The collection and detection system includes a control module configured to control the processing of the fluid sample such that detection of one or more types of particles is fully automated within the integrated cartridge. The types of particles to be processed and detected include, but are not limited to, cells, bacteria, viruses, nucleic acids, toxins, and other pathogens. If one or more specific types of particles are detected, a system alarm is triggered. In some embodiments, the system alarm is an alarm signal which is transmitted over a communications network to either a local or central monitoring location. More than one collection and detection system can be coupled to the network and monitored by the central monitoring location. In other embodiments, the system alarm is an audio and/or visual signal generated by the collection and detection system itself.

FIG. 1 illustrates an exemplary network configuration including multiple collection and detection systems 10. Each collection and detection system 10 can be operated independently, or networked to a remote monitoring location, as is illustrated in FIG. 1. The monitoring location can be local, as in the local monitoring point 40, or centralized, such as the central monitoring point 50. As shown in FIG. 1, each collection and detection system can operate independently, can be coupled to a local monitoring point, which in turn can be coupled to a central monitoring point, or can be coupled to the central monitoring point. The collection and detection system 10 is coupled to the local monitoring point 40 or the central monitoring point 50 via any conventional network 60. Network connectivity also enables remote control signal to be provided to the collection and detection system 10.

Figure 2:
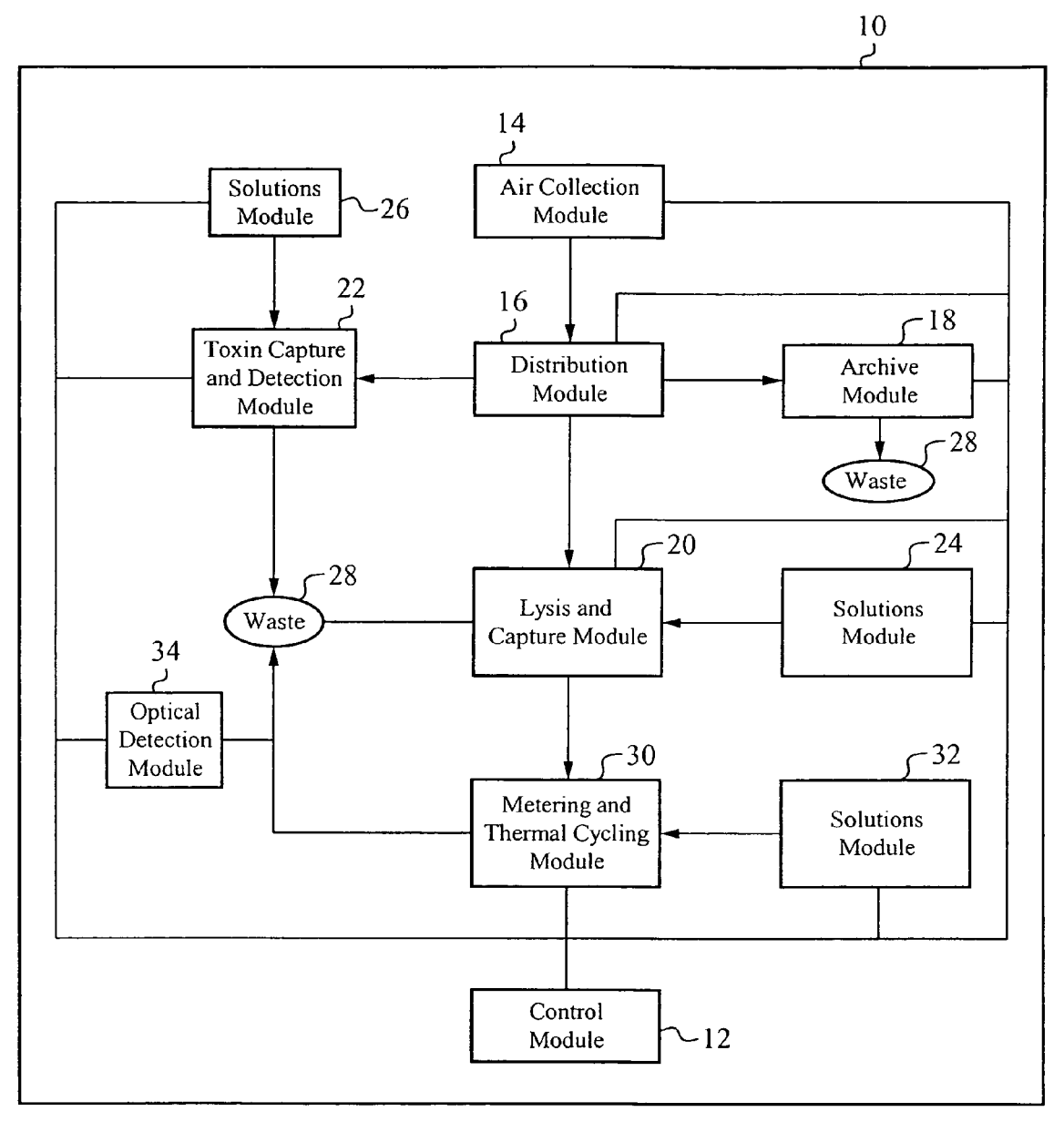

A first embodiment of the integrated collection and detection system is directed to a detect to treat system in which specific particles are identified. FIG. 2 illustrates an exemplary functional block diagram of the first embodiment of the integrated collection and detection system. The integrated collection and detection system 10 includes a control module 12, an air collection module 14, a distribution module 16, an archive module 18, a lysis and capture module 20, a toxin capture and detection module 22, a solutions module 24, a solutions module 26, a waste module 28, a metering and thermal cycling module 30, a solutions module 32, and an optical detection module 34. Fluid is directed between modules and within each module using microfluidic pathways and valves, also referred to as microfluidic circuitry.

The air collection module 14 is configured to intake ambient air and collect airborne particles within the air. Air is collected for a predetermined time frame, after which the collected particles are eluted into a liquid sample which is output from the air collection module 14. The fluid sample output from the air collection module 14 includes a fluid and particle solution.

The distribution module 16 meters and distributes the fluid sample output from the air collection module 14. The fluid sample is metered and distributed according to predetermined ratios. A first portion of the fluid sample is directed to the archive module 18, a second portion to the lysis and capture module 20, and a third portion to the toxin capture and detection module 22. In one embodiment, a syringe pump is used as part of the microfluidic circuitry to meter the fluid sample. A syringe pump is adaptable for changing applications, such as changing the distribution ratio from one application to the next. In another embodiment, a reservoir with drain holes is included as part of the microfluidic circuitry. The location of each drain hole corresponds to a desired distribution ratio. A valve is coupled to the drain line of each drain hole to control the collection and distribution of the fluid sample between runs. Such a configuration is appropriate where the distribution ratio is fixed, as the location of the drain holes is a fixed specification. In yet another embodiment, aspects of a fixed ratio configuration, such as the reservoir with drain holes, is combined with aspects of the adjustable ratio configuration, such as the syringe pump. It is understood that other microfluidic circuit configurations can be used to meter and distribute the fluid samples for both fixed and variable distribution ratios.

The archive module 18 is configured to store one or more fluid samples. The fluid samples are stored for later analysis and/or confirmation, if necessary. The lysis and capture module 20 is configured to perform a lysis, purification, and concentration process on the fluid sample received from the distribution module 16. Lysis is performed on cells within the received fluid sample that are capable of being lysed. Lysis is performed using sonication. Alternatively, any conventional lysis method can be used. Once the cells are lysed, the resulting nucleic acids are purified and concentrated to be sent to the metering and thermal cycling module 30. The solutions module 24 provides solutions used during the lysis, purification, and concentration steps performed in the lysis and capture module 20. For example, the solutions module 24 includes wash solutions and elution buffers.

The metering and thermal cycling module 30 receives the concentrated fluid sample from the lysis and capture module 20. The received fluid sample is metered and distributed into a predetermined number of collection vessels. The metering and thermal cycling module 30 is coupled to the solutions module 32 to receive mixing solution that is metered and distributed to each collection vessel such that a combination of concentrated fluid sample and mixing solution are temporarily stored in each collection vessel. Each collection vessel is coupled to a corresponding thermal cycling chamber to successively heat and cool the combined solution. In this manner, the fluid sample and mixing solution combination within each collection vessel undergoes a thermal cycling process within the thermal cycling chambers to amplify any nucleic acids present in the fluid sample. Any number of thermal cycles can be performed. This amplification process can be repeated, for example a pre-amplification step and an amplification step can be performed.

The amplified fluid sample from each thermal cycling chamber is successively output from the metering and thermal cycling module 30. Each amplified fluid sample output from the metering and thermal cycling module 30 is interrogated by the optical detection module 34. In general, any conventional luminescence detection technology can be applied to perform biological detection. The raw data obtained by the optical detection module 34 is provided to the control module 12, where it is used to determine the presence of one or more types of nucleic acids. If a nucleic acid is detected, the control module 12 generates an alarm signal. Alternatively, the raw data collected by the optical detection module 34 is sent to a remote location, such as the central monitoring point 50 (FIG. 1) for analysis.

The toxin capture and detection module 22 is configured to capture toxins present in the fluid sample received from the distribution module 16. The toxin capture and detection module 22 is also configured to detect the presence of any captured toxins using any conventional luminescence detection technology. The raw data obtained by the toxin capture and detection module 22 is provided to the control module 12, where it is used to determine the presence and identity of one or more specific types of toxins. If a specific toxin is detected, the control module 12 generates an alarm signal. Alternatively, the raw data collected by the toxin capture and detection module 22 is sent to a remote location, such as the central monitoring point 50 (FIG. 1) for analysis. In one embodiment, the toxin capture and detection module 22 includes an optical detection device configured to measure one or more characteristics of any captured toxin. The solutions module 26 provides solutions used during the toxin capture steps performed in the toxin capture and detection module 22. For example, the solutions module 26 includes wash solutions and antibody solutions.

The collection and detection system 10 is configured to be re-used such that successive fluid samples output by the air collection module 14 are processed. As such, the distribution module 16, the lysis and capture module 20, the toxin capture and detection module 22, the metering and thermal cycling module 30, and all interconnecting microfluidic circuitry including the microfluidic circuitry coupling the metering and thermal cycling module 30 and the optical detection module 34 are decontaminated between cycles. Various solutions are used to perform the rinse and wash steps during decontamination, these solutions are included in the solutions module 24 and the solutions module 26.

The control module 12 is coupled to each module to control operation of the collection and detection system 10. Such control enables complete automation of the collection and detection process, without need of human intervention. The control module 12 is also configured to analyze the raw data provided by the toxin capture and detection module 22 and the optical detection module 24, and to generate any appropriate alarm signals. In response to an alarm signal, the control module 12 initiates a localized audio and/or visual alarm and/or transmits a notification signal to a networked local monitoring location or a centralized monitoring location.

The analyzed fluid samples, elution buffers, mixing solutions, rinses, washes, purged archive samples, and other solutions related to the processing of fluid samples and subsequent decontamination of the collection and detection system 10 are directed to the waste module 28. Alternatively, fluid samples analyzed and subsequently output by the toxin capture and detection module 22 and the optical detection module 34 can be archived, either in the archive module 18, or a supplemental archive module (not shown). The embodiments of the particle collection and detection module 10 described above include three solutions modules. Alternatively, one or more of the solutions modules 24, 26, and 32 can be combined, or more than three solutions modules can be used.

The system implementation illustrated in FIG. 2 is for illustrative purposes. The microfluidic circuitry and module nature of the integrated collection and detection system provides flexibility and extensibility to interconnect and configure the modules, and associated sub-modular components, into any desired combination. For example, the fluid sample can be metered into additional portions, and each portion can be further sub-divided into smaller portions. These portions can be distributed to any one of a multitude of fluid processing pathways, including the fluid pathway through the lysis and capture module 20 and the metering and thermal cycling module 30, the fluid pathway through the toxin capture and detection module 22, and any other fluidic pathway configured according to one or more of the modules and/or sub-modules described above. As an additional example, a lysis module similar to the lysis component in the lysis and capture module 20 can be added prior to the toxin capture and detect module 22 to lyse cells prior to delivering the fluid sample to the toxin capture and detect module 22. Similar parallel pathways can also be configured such that a portion of the fluid sample is received unlysed by the toxin capture and detect module 22, and another portion of the fluid sample is first lysed by a lysis component and then the lysed sample is delivered to another toxin capture and detect module. Additionally, the specific configurations described for each of the modules is for exemplary purposes. The microfluidic circuitry and constituent components of each module can be adapted into any number of configurations to perform the described functionality.

Figure 3:
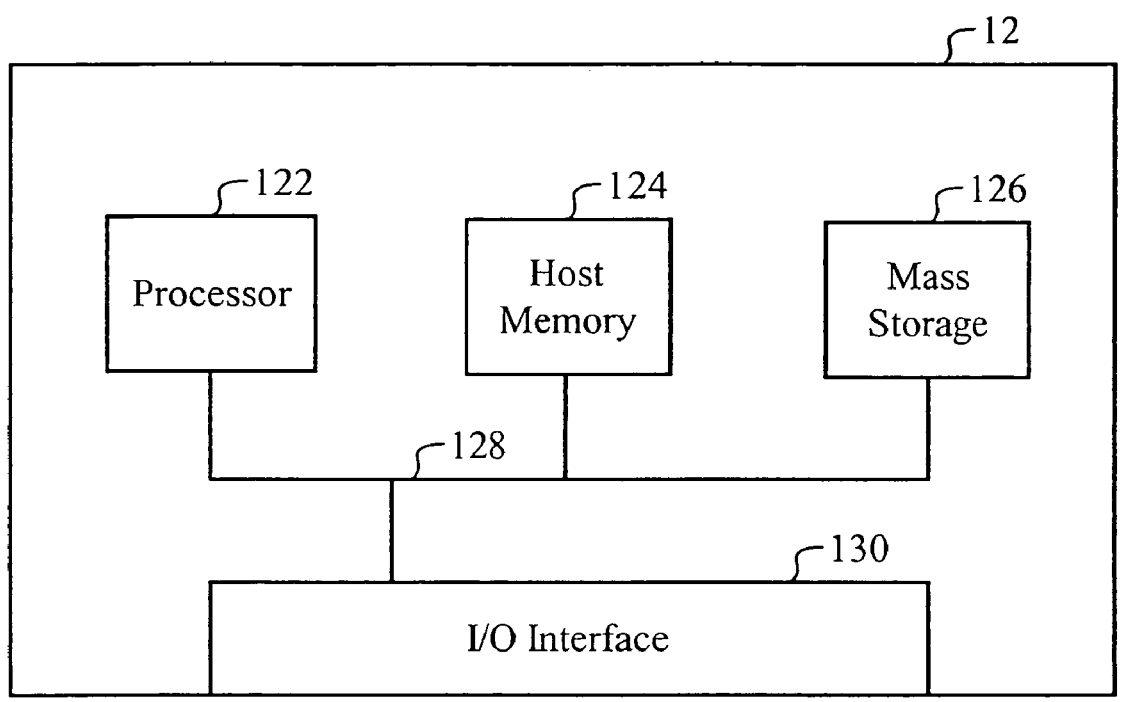
FIG. 3 illustrates an exemplary block diagram of the control module.

FIG. 3 illustrates an exemplary block diagram of the control module 12. The control module 12 includes a processor 122, a host memory 124, a mass storage 126, and an I/O interface 130, all coupled via a system bus 128. The mass storage 126 can include both fixed and removable media using any one or more of magnetic, optical or magneto-optical storage technology or any other available mass storage technology. The host memory 124 is a random access memory (RAM). The processing module 122 is configured to control the operation of the collection and detection system 10. The I/O interface 130 includes a user interface and a network interface. In some embodiments, the user interface includes a display to show user instructions and feedback related to input user commands. The network interface includes a physical interface circuit for sending and receiving data and control communications over a conventional network, such as to a local or centralized monitoring location.

Figure 4:
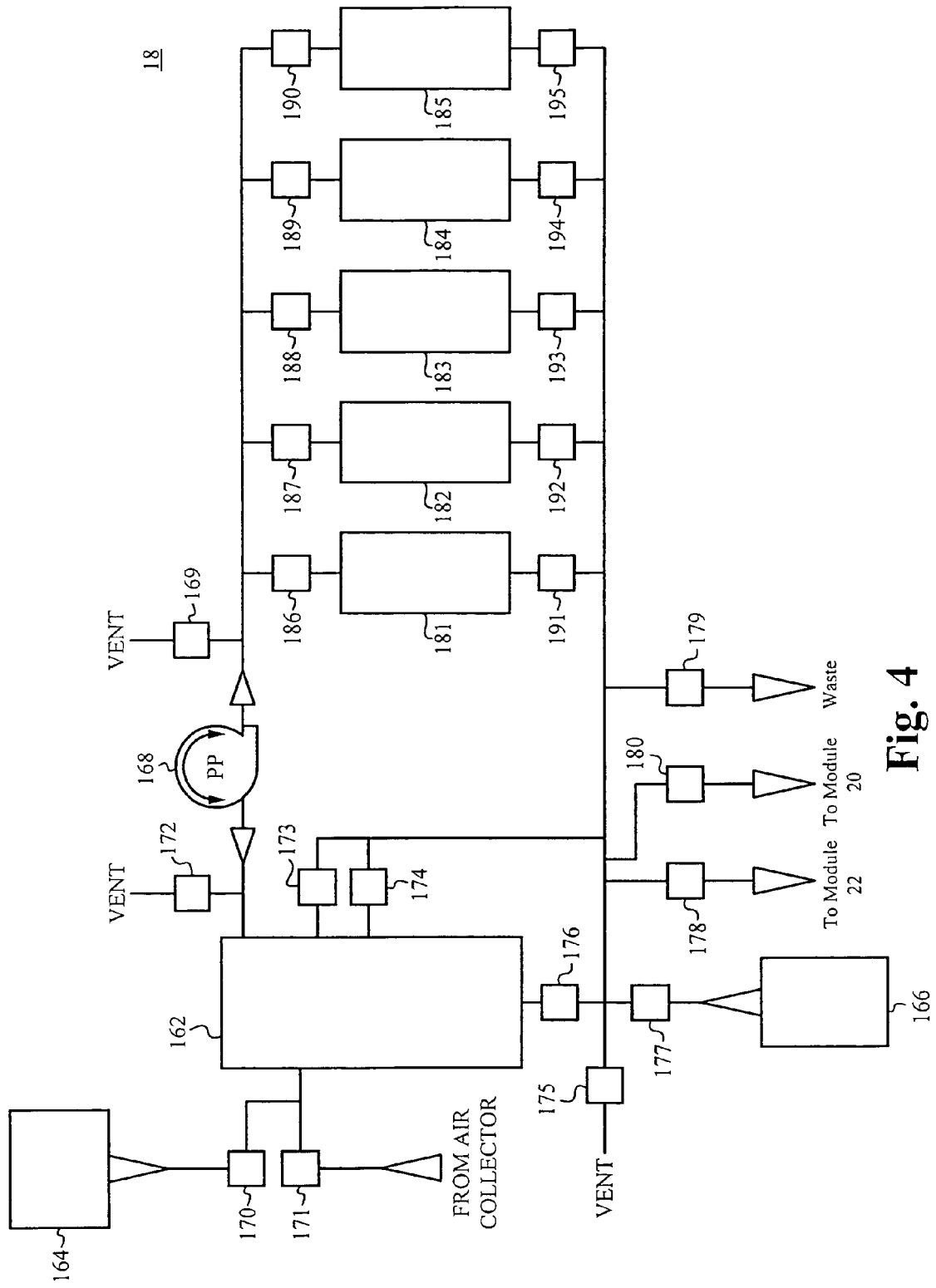
FIG. 4 illustrates an exemplary schematic diagram of the archive module.

FIG. 4 illustrates an exemplary schematic diagram of the distribution module 16 coupled to the archive module 18. In this exemplary configuration, the distribution module 16 includes a metering module 162, a wash syringe 164, a syringe pump 166, and a peristaltic pump 168 coupled together via microfluidic circuitry including valves 169-180. The archive module 18 includes five archive chambers 181-185 coupled to the distribution module 16 via microfluidic circuitry including the valves 186-195.

The fluid sample provided by the air collection module 14 is stored in the metering module 162. In general, the amount of fluid sample provided by the air collection module 14 is an inconsistent amount. In one embodiment, the collection and detection system 10 is configured to process a specific amount of fluid sample, in this case 10 ml. As such, a first step is to remove excess fluid sample from the metering module 162. As applied to the configuration of FIG. 4, any excess fluid sample is removed from the metering module 162 by opening the valve 173 and the valve 179, which enables any excess fluid sample to flow to waste. Remaining is the specific amount of fluid sample in the metering module 162.

Each archive chamber 181-185 is configured to store a predetermined amount of fluid sample. In one embodiment, each archive module 181-185 is configured to store 1 ml. This predetermined amount of fluid sample is metered from the metering module 162 and delivered to one of the archive chambers 181-185 by opening the valves 174 and 169 and the valves corresponding to the archive chamber, such as the valves 186 and 191 for archive chamber 181, turning on the peristaltic pump 168 in a first direction, which forces air from the vent at the valve 169 into the metering module 162. This pressurizes the metering module 162 thereby forcing the fluid sample within through the open valves 174 and 191 and into the archive module 181.

One archive chamber stores the fluid sample for the current cycle, and the remaining four archive chambers store the fluid samples from the previous four cycles. During the next cycle, the oldest fluid sample in the archive is removed and replaced by the next fluid sample. For example, during a first cycle, a first fluid sample is received from the distribution module 16 and stored in the archive chamber 181. During a second cycle, a second fluid sample is received and stored in the archive chamber 182. During a third cycle, a third fluid sample is received and stored in the archive chamber 183. During a fourth cycle, a fourth fluid sample is received and stored in the archive chamber 184. During a fifth cycle, a fifth fluid sample is received and stored in the archive chamber 185. During a sixth cycle, the first fluid sample stored in the archive chamber 181 is first purged to waste. To purge the fluid sample from the archive chamber 181, the valves 172, 186, 191, and 179 are opened and the peristaltic pump 168 is run in a second direction, which forces air from the vent at the valve 172 into the archive chamber 181. This pressurizes the archive chamber 181 thereby forcing the fluid sample within through the open valves 191 and 179 to waste. The valves 172, 186, 191, and 179 are then closed and the archive chamber 181 is then washed using solution provided via the wash syringe 164. The sixth fluid sample is then provided from the distribution module 16 to the empty archive chamber 181. Subsequent fluid samples are stored in a similar manner such that the most recent five fluid samples are archived in the archive module 18.

After the first portion of the fluid sample in the metering module 162 is archived, the remaining fluid sample is metered and distributed to the toxin capture and detection module 22 and the lysis and capture module 20. To meter and distribute a second portion of the fluid sample to the toxin capture and detection module 22, the valves 172, 176, and 177 are opened and the syringe pump 166 is turned on in a first direction to intake the second portion through the open valves 176 and 177 into the syringe pump 166. The valves 172 and 176 are then closed, the valve 177 remains open, and the valve 178 is opened. The syringe pump 166 is turned on in a second direction to force the second portion of the fluid sample from the syringe pump 166 through the open valves 177 and 178 to the toxin capture and detection module 22.

To meter and distribute a third portion of the fluid sample to the lysis and capture module 20, the valves 172, 176, and 177 are opened and the syringe pump 166 is turned on in the first direction to intake the third portion through the open valves 176 and 177 into the syringe pump 166. The valves 172 and 176 are then closed, the valve 177 remains open, and the valve 180 is opened. The syringe pump 166 is turned on in the second direction to force the third portion of the fluid sample from the syringe pump 166 through the open valves 177 and 180 to the lysis and capture module 20. The syringe pump 166 is programmable to withdraw any amount of fluid sample as is required by the application. This adds flexibility in determining how much fluid sample is provided to the toxin capture and detection module 22 and the lysis and capture module 20. In one embodiment, the second portion of fluid sample is 3 ml and the third portion of fluid sample is 6 ml.

Although the archive module is shown in FIG. 4 as including five archive chambers, the archive module can be configured to include more or less than five archive modules. Further, the archiving methodology described above is for exemplary purposes only and any conventional methodology can be used to purge and store subsequent fluid samples. Still further, the metering and distribution configuration and methodology described above in relation to FIG. 4 is but one embodiment. It is understood that other configurations and methodologies are contemplated for metering and distributing any number of fluid sample portions in any denomination.

Figure 5:
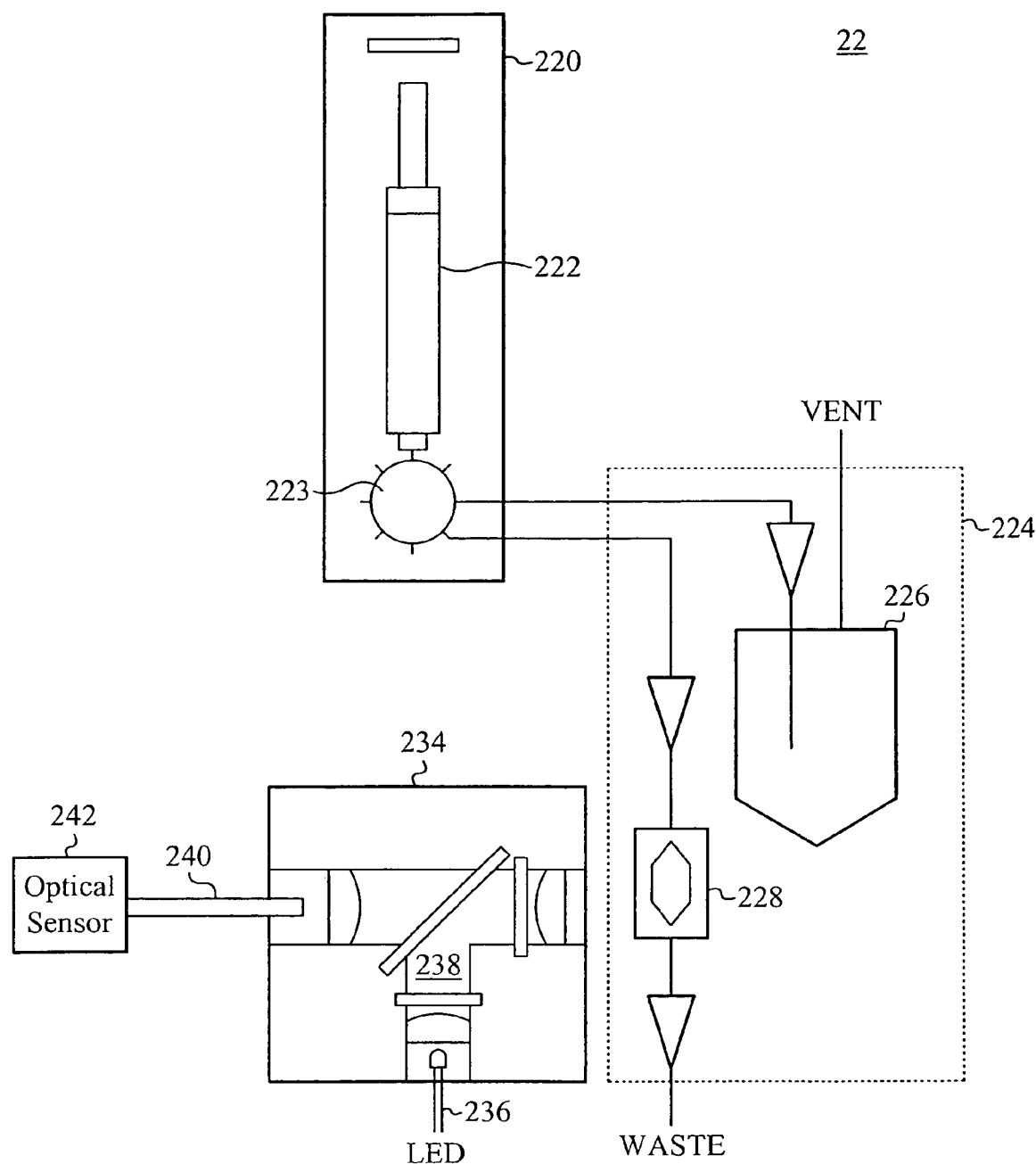
FIG. 5 illustrates an exemplary schematic diagram of the toxin capture and detection module.

FIG. 5 illustrates an exemplary schematic diagram of the toxin capture and detection module 22. The toxin capture and detection module 22 includes a pump assembly 220 including a syringe pump 222 and a distribution valve 223, a capture module 224, and an optical detection module 234. The capture module 224 includes a capture device 228 and a reservoir 226. The fluid sample provided by the distribution module 16 is received by the distribution valve 223 and directed to the capture module 224, where the fluid sample flows through the capture device 228. The distribution valve 223 is also connected to one or more reagent vessels within the solutions module 26.

In one embodiment, the capture device 228 is a capture chip including a plurality of pillars configured such that fluid flows around the pillars making contact therewith. The pillars are prepared such that specific toxins within the fluid sample adhere to the surface of the pillars as the fluid flows past. The fluid sample flows through the capture chip 228 and outputs the capture module 224 to waste, while any of the specific toxins present in the fluid sample remain in the capture chip 228. In one embodiment, each pillar is pre-coated with a particular antibody. Each antibody adheres to a particular type of toxin. When the fluid sample flows past the pillars, the specific toxin present within the fluid sample adheres to the antibody on the pillars. An example of the capture chip 228 is described in U.S. Pat. Nos. 5,707,799 and 5,952,173, which are both hereby incorporated by reference.

In alternative embodiments, the pillars are pre-coated with more than one type of antibody such that each capture chip captures more than one different type of toxin. More than one capture chip can be coupled in series or in parallel to further diversify and expand the different types of toxins collected. For example, a first capture chip in a sequence is pre-coated with a first antibody, a second capture chip in the sequence is pre-coated with a second antibody, and so on for as many capture chips in the series. Additionally, one, some, or all of the capture chips in the series can be pre-coated with more than one antibody. For example, a capture chip can be pre-coated with multiple antibodies. Each antibody to adhere to a specific type of toxin. The different captured toxins can then be distinguished according to a distinguishing characteristic, such as different optical wavelengths. In a series configuration, the fluid sample flows in series from the first capture chip to the second capture chip and so on. Although the capture device 228 is described above as a capture chip, the capture device 228 can be any conventional device capable of capturing one or more toxins.

The toxin capture and detection module 22 includes the optical detector 234 coupled to the capture device 228. The capture device 228 is configured such that the toxin captured within is optically accessible to the optical detector 234. In one embodiment, the capture device 228 includes an optically transparent lid. Alternatively, the captured toxin is eluted from the capture device 228 and collected in a separate collection means, such as a vessel or reservoir. Optical detection can then be performed on the eluted toxin in the collection means.

In this embodiment, the optical detector 234 includes a light source 236, such as an LED or a laser, an optical pathway 238, such as one or more lenses, filters and beam splitters, a fiber optics 240, and an optical sensor 242. The optical detector 234 is configured to direct light onto the capture device 228, and to collect and measure characteristics of the light reflected back. The characteristics of the reflected light are used to identify the toxin(s) captured in the capture device 228. The configuration of the optical detector 234 shown in FIG. 5 is for exemplary purposes only. In some embodiments, the optical detector 234 is configured to include a light source, an optical pathway to direct the light onto a specific location of the capture device 228 and to direct the reflected light from the capture device 228 to an optical detector, and the optical detector. In other embodiments, a light source is not included. In such cases, light is emitted from the captured toxins, such as by chemi-luminescence. The emitted light is detected by the optical sensor. In one embodiment, the optical detector is any conventional optical detection device capable of measuring one or more disparate wavelengths. The measured characteristics are provided from the optical detector 234 to the control module 12 for analysis.

In some embodiments, a toxin captured in the capture device 228 is identified by forming a sandwich assay, including a flourescent marker, and then detecting the flourescent marker. The flourescent marker is optically detectable using the optical detector 234. Each type of toxin is associated with a specific type of flourescent marker. It is understood that other conventional means for marking and identifying the toxin can be used.

Once the captured toxins are interrogated by the optical detector 234, the capture device 228 is washed using washing solutions provided from the solutions module 26 and directed to the capture device 228. The washing solutions are received from the solutions module 26 by the distribution valve 223.

Where the capture device 228 comprises multiple capture devices coupled in series, each device in series is coupled to a corresponding optical detector of the type described above.

Figure 6:
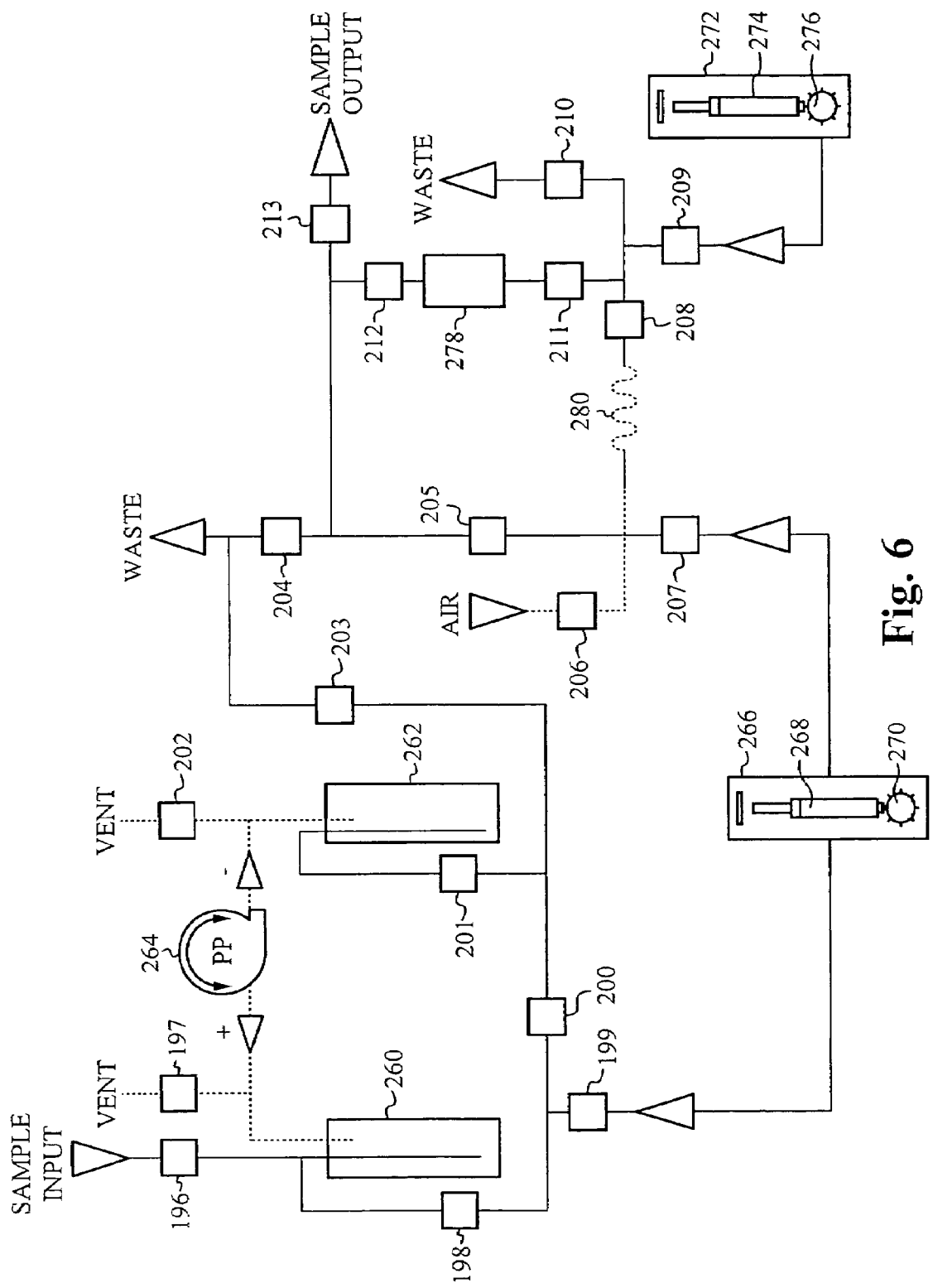
FIG. 6 illustrates an exemplary schematic diagram of the lysis and capture module.

FIG. 6 illustrates an exemplary schematic diagram of the lysis and capture module 20. The lysis and capture module 20 is configured to lyse cells present in the fluid sample, and to capture the nucleic acids of the lysed cells. The lysis and capture module 20 includes a lysis chamber 260, a mixing chamber 262, a peristaltic pump 264, a pump assembly 266 including a syringe pump 268 and a distribution valve 270, a pump assembly 272 including a syringe pump 274 and a distribution valve 276, a purification device 278, a cooling element 280, such as a thermal electric cooler, and valves 196-213. The microfluidic circuitry including the peristaltic pump 264, the pump assembly 266, the pump assembly 272, and the valves 196-213 are configured to direct the fluid sample through the lysis and capture module 20, as well as to direct the various solutions used in processing and decontamination. The mixing chamber 262 is configured for mixing and holding solutions. For example, in some applications, one or more additional solutions are added to the fluid sample prior to lysing, and/or one or more additional solutions are added after lysing.

The peristaltic pump 264 is configured to pressurize either the lysis chamber 260, which forces fluid from the lysis chamber 260 to the mixing chamber 262, or to pressurize the mixing chamber 262, which forces fluid from the mixing chamber 262 to the lysis chamber 260. During either operation, the appropriate valves are opened to enable such fluid flow.

The fluid sample provided by the distribution module 16 is directed to the lysis chamber 260. In one embodiment, lysis is performed using sonication. In some embodiments, selective lysis is performed where specific types of cells are lysed at different sonication energies. In this embodiment, the lysis and capture module 20 is configured to selectively lyse a specific type of cell at a corresponding sonication energy. The lysed cells are then separated from the fluid sample. Additional sonication steps can be performed on the remaining fluid sample to selectively lyse one or more additional cell types. An exemplary apparatus and method for performing such a selective lysis process is described in the co-pending and co-owned U.S. patent application Ser. No. 10/943,601, filed on Sep. 17, 2004, and entitled "Microfluidic Differential Extraction Cartridge," which is hereby incorporated in its entirety by reference. Alternatively, other conventional lysis methods are utilized, such as heating and/or chemical treatment.

The pump assembly 266 is configured to direct the lysed fluid sample through the cooling element 280 and the purification device 278 to waste via the valve 204. Nucleic acid within the lysate is purified and concentrated as the lysate flows through the purification device 278.

In one embodiment, the purification device 278 is a purification chip including a plurality of pillars configured such that fluid flows around the pillars making contact therewith. Nucleic acid is known to be attracted to silicon. In one embodiment, the pillars within the purification chip are comprised of silicon such that as the fluid flows past the pillars, nucleic acid within the fluid adheres to the pillars. Alternatively, the pillars are comprised of a material other than silicon and are coated with silicon. Still alternatively, the pillars are comprised of or coated with a material to which nucleic acid adheres. The fluid sample flows through the purification chip 278 and outputs the lysis and capture module 20 to waste, while nucleic acid present in the fluid sample remains in the purification chip 278. An example of the purification chip 278 is also described in U.S. Pat. Nos. 5,707,799 and 5,952,173. More than one purification chip 278 can be coupled in series or in parallel. In a series configuration for example, the fluid sample flows from a first purification chip in the series to a second purification chip and so on. Although the purification device 278 is described above as a purification chip, the purification device 278 can be any conventional device capable of capturing nucleic acid.

The pump assembly 266 is also configured to direct a wash solution through the purification device 278 to remove residual fluid sample solution. The wash solution is provided from the solutions module 24 via the distribution valve 270 and is directed to waste via the valve 84. Air is then blown through the purification device 228 to remove residual wash solution. The captured nucleic acids are removed from the purification device 278 using an elution buffer. The pump assembly 272 is configured to direct the elution buffer from the solutions module 24 through the purification device 278 to elute the nucleic acid. A purified and concentrated nucleic acid solution is output from the purification device 278 and output from the lysis and capture module 20 via the valve 213. In one embodiment, a heating element (not shown) is coupled to the purification device 278. Prior to eluting the nucleic acid from the purification device 278, the heating element heats the purification device 278, which facilitates the elution process.

The lysis and capture module 20 is also configured to back-flush the purification device 278, either to un-block the device or as part of wash and decontamination process. The microfluidic circuitry is configured to direct wash solution backwards through the purification device 278 and out to waste via the valve 210.

Figure 7:
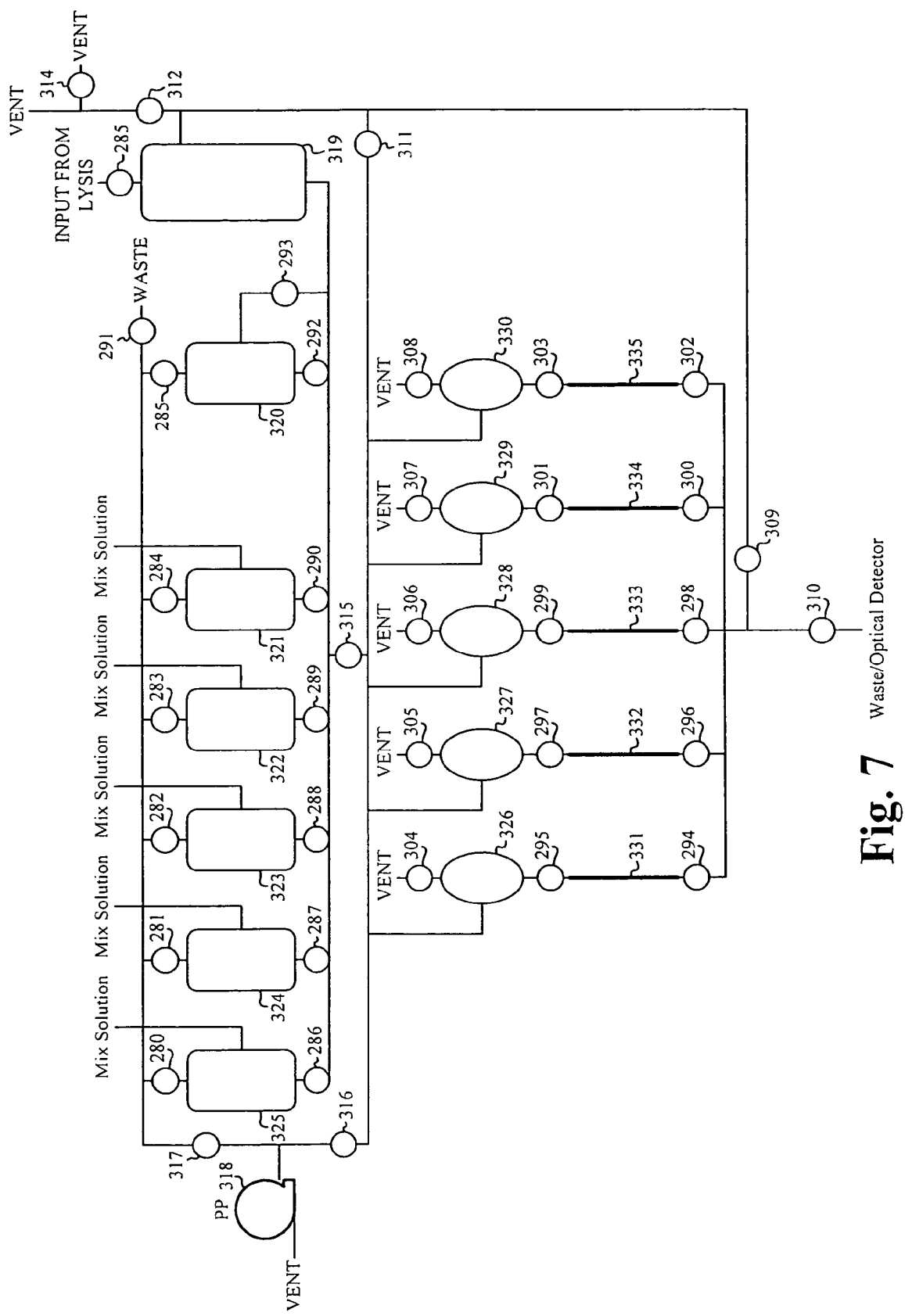
FIG. 7 illustrates an exemplary schematic diagram of the metering and thermal cycling module.

FIG. 7 illustrates an exemplary schematic diagram of the metering and thermal cycling module 30. The metering and thermal cycling module 30 is configured to preamplify and amplify any nucleic acid present in the nucleic acid solution provided by the lysis and capture module 20. The metering and thermal cycling module 30 is also configured to tag one or more specific types of nucleic acids if present within the amplified nucleic acid solution. The one or more specific acids are tagged using a conjugated antibody solution including a different flourescent marker for each specific nucleic acid. The metering and thermal cycling module 30 includes a plurality of solution reservoirs 321-325, a holding reservoir 319, a metering reservoir 320, a plurality of valves 280-317, a peristaltic pump 318, a plurality of thermal cycling chambers 331-335, and a plurality of mixing reservoirs 326-330.

Each of the plurality of solution reservoirs 321-325 are coupled to the solutions module 32 and are configured to store a specific amount of master mix solution received from the solutions module 32. The holding reservoir 319 is configured to store the nucleic acid solution output from the lysis and capture module 20. The metering reservoir 320 is configured to meter and to store a specific amount of the nucleic acid solution from the holding reservoir 319. In one embodiment, each of the solution reservoirs 321-325 are configured to store 15 ul, and the metering reservoir is configured to store 10 ul. A first metered portion of the nucleic acid solution is directed from the fluid metering reservoir 320 to the mixing reservoir 326, and the specific amount of mixing solution from the holding reservoir 325 is directed to the mixing reservoir 326. A second portion of the nucleic acid solution is then metered and stored in the metering reservoir 320. The second metered portion is directed from the metering reservoir 320 to the mixing reservoir 327, and the specific amount of mixing solution from the holding reservoir 324 is directed to the mixing reservoir 327. A metered portion of the nucleic acid solution and a specified amount of the mixing solution is provided to each of the remaining mixing reservoirs 328-330 in a similar manner.

The mixed solution in the mixing reservoir 326 is directed to the thermal cycling chamber 331, the mixed solution in the mixing reservoir 327 is directed to the thermal cycling chamber 332, the mixed solution in the mixing reservoir 328 is directed to the thermal cycling chamber 333, the mixed solution in the mixing reservoir 329 is directed to the thermal cycling chamber 334, and the mixed solution in the mixing reservoir 330 is directed to the thermal cycling chamber 335. A heating element (not shown) is coupled to each of the thermal cycling chambers to perform a thermal cycling process. In one embodiment, the thermal cycling chambers 331-335 are configured as elongated tubes capped at a each end by a valve, and the tubes are coupled to a heating mesh to form a heating and tube assembly. An example of such a heating and tube assembly is described in the co-owned and co-pending U.S. patent application Ser. No. 11/201,615, filed on Aug. 10, 2005, and entitled "Disposable Integrated Heater and Tube Assembly for Thermally-driven Chemical Reactions," which is hereby incorporated by reference.

The microfluidic circuitry within the metering and thermal cycling module 30 is configured such that multiple different thermal cycling processes can be performed. After a first thermal cycling process is performed on a first mixed solution, as described above, the resulting solutions in the thermal cycling chambers 331-335 are back-flushed into the corresponding mixing reservoirs 326-330. Alternatively, additional microfluidic circuitry is provided which directs solutions from the thermal cycling chambers 331-335 to their respective mixing reservoirs 326-330. Additional mixing solutions can be provided to the mixing reservoirs 326-330 from the solution reservoirs 321-325. The mixing solutions provided during this step can be the same or different than the mixing solutions provided during the first thermal cycling process. The mixed solutions are then directed back to the thermal cycling chambers 331-335 for a second thermal cycling process. Additional thermal cycling processes can be performed in this manner. In one application, a pre-amplification process is performed during the first thermal cycling process and an amplification process is performed during the second thermal cycling process. An example of one such pre-amplification and amplification process is described in the co-pending, co-owned U.S. patent application Ser. No. 11/509,868, filed Aug. 24, 2006, and entitled "A Method for Detecting Multiple Limited Copy Targets, which is hereby incorporated by reference. The amplification process results in an amplified nucleic acid solution. The amplified nucleic acid solution is output from the metering and thermal cycling module 30.

One or more additional processing steps can be performed on the amplified nucleic acid solution prior to being output from the metering and thermal cycling module 30. Such additional processing steps prepare the amplified nucleic acid solution for interrogation by the optical detection module 34. The amplified nucleic acid solution is back-flushed from the thermal cycling chambers 331-335 to the corresponding mixing reservoirs 326-330. An additional solution is added to each of the mixing reservoirs. The additional solution is configured to adhere to one or more specific types of nucleic acids if present within the amplified nucleic acid solution. The resulting product includes a different flourescent marker for each specific nucleic acid. This product is then output from the metering and thermal cycling module 30. It is understood that alternative chemistries can be used to detect the presence of the specific types of nucleic acids.

Although the metering and thermal cycling module 30 shown in FIG. 7 is configured with five thermal cycling chambers, five mixing reservoirs, and five solution reservoirs, the metering and thermal cycling module 30 can be configured with more or less than five thermal cycling chambers, five mixing reservoirs, and five solution reservoirs. Still alternatively, an alternative mixing method eliminates the mixing reservoirs and relies on mixing within the fluid lines themselves during transport of the fluids from the solutions reservoirs to the thermal cycling chambers.

Figure 8:
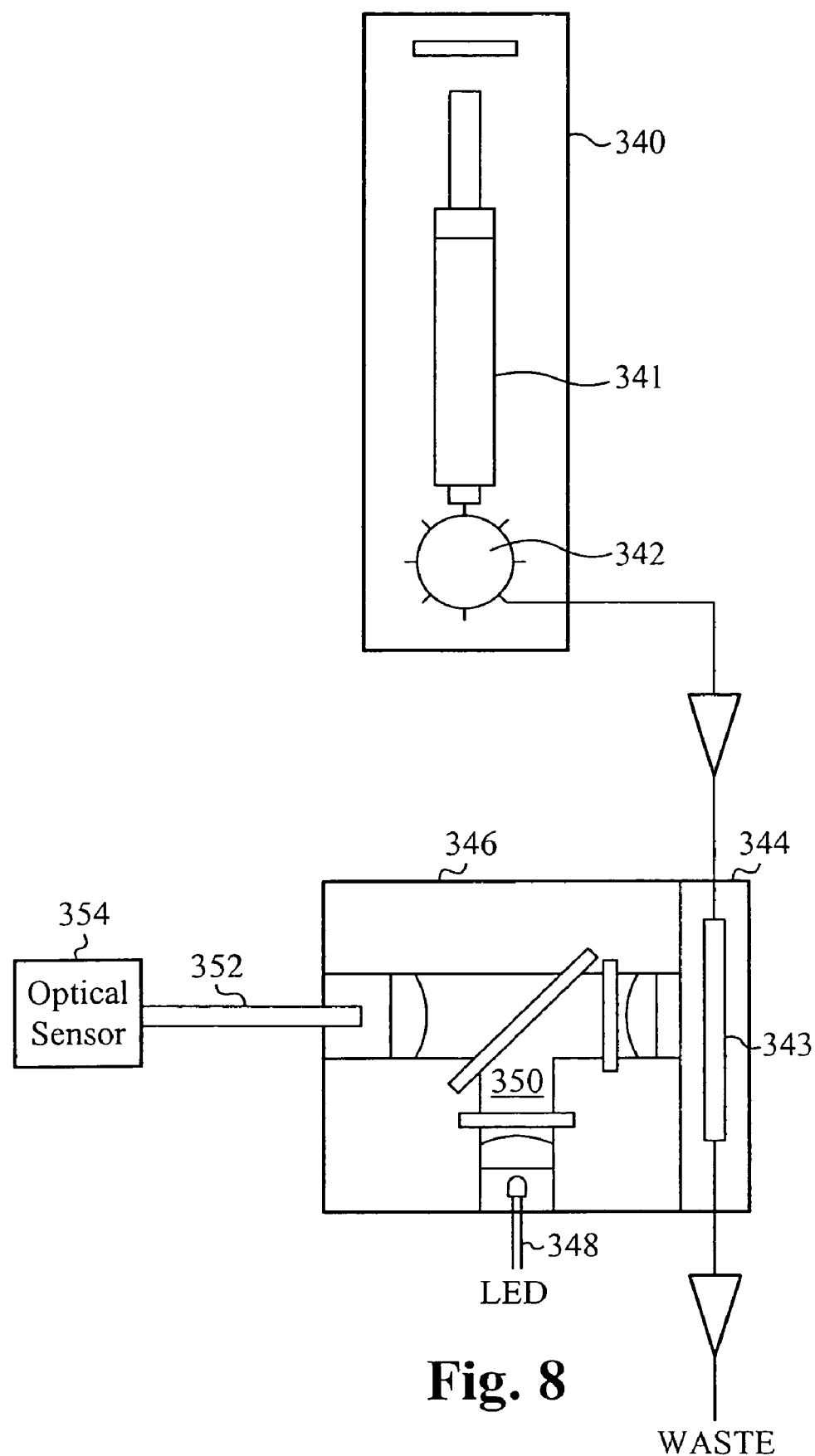
FIG. 8 illustrates an exemplary schematic diagram of the optical detection module.

FIG. 8 illustrates an exemplary schematic diagram of the optical detection module 34. The optical detection module 34 includes a pump assembly 340 including a syringe pump 341 and a distribution valve 342, a fluid line 344 including an interrogation channel 343, and an optical detector 346. The fluid line 344 receives the amplified nucleic acid solution output from the metering and thermal cycling module 30. The interrogation channel 343 is an optically transparent portion of the fluid line 344 that enables optical analysis to be performed by the optical detector 346 as the amplified nucleic acid solution passes through the optically transparent portion. In one embodiment, the interrogation channel 343 is integrated within the microfluidic circuitry connecting the metering and thermal cycling module 30 to the waste module 28 (FIG. 2). In this configuration, optical measurements are taken of the amplified nucleic acid solution as the solution is directed to waste. Alternatively, a collection vessel is coupled to the fluid line 344, and the amplified nucleic acid solution is collected in the collection vessel, where optical measurements are taken.

The optical detector 346 includes a light source 348, such as a white-light LED or a laser, an optical pathway 350, such as one or more lenses, filters and beam splitters, a fiber optics 352, and an optical sensor 354. The optical detector 346 is functionally equivalent to the optical detector 234 (FIG. 5) in the toxin capture and detect module 22. The optical detector 346 is configured to direct light into the interrogation channel 343, and to collect and measure characteristics of the light reflected back. The characteristics of the reflected light are used to determine if specific types of nucleic acids are present in the amplified nucleic acid solution. The configuration of the optical detector 346 shown in FIG. 8 is for exemplary purposes only. In some embodiments, the optical detector 346 is configured to include a light source, an optical pathway to direct the light onto the interrogation channel 343 and to direct the reflected light from the interrogation channel 343 to an optical detector, and the optical detector. In other embodiments, a light source is not included. In such cases, light is emitted from the captured toxins, such as by chemi-luminescence. The emitted light is detected by the optical sensor. In one embodiment, the optical detector is any conventional optical detection device capable of measuring one or more disparate wavelengths. The measured characteristics are provided from the optical detector 346 to the control module 12 for analysis.

Figure 9:
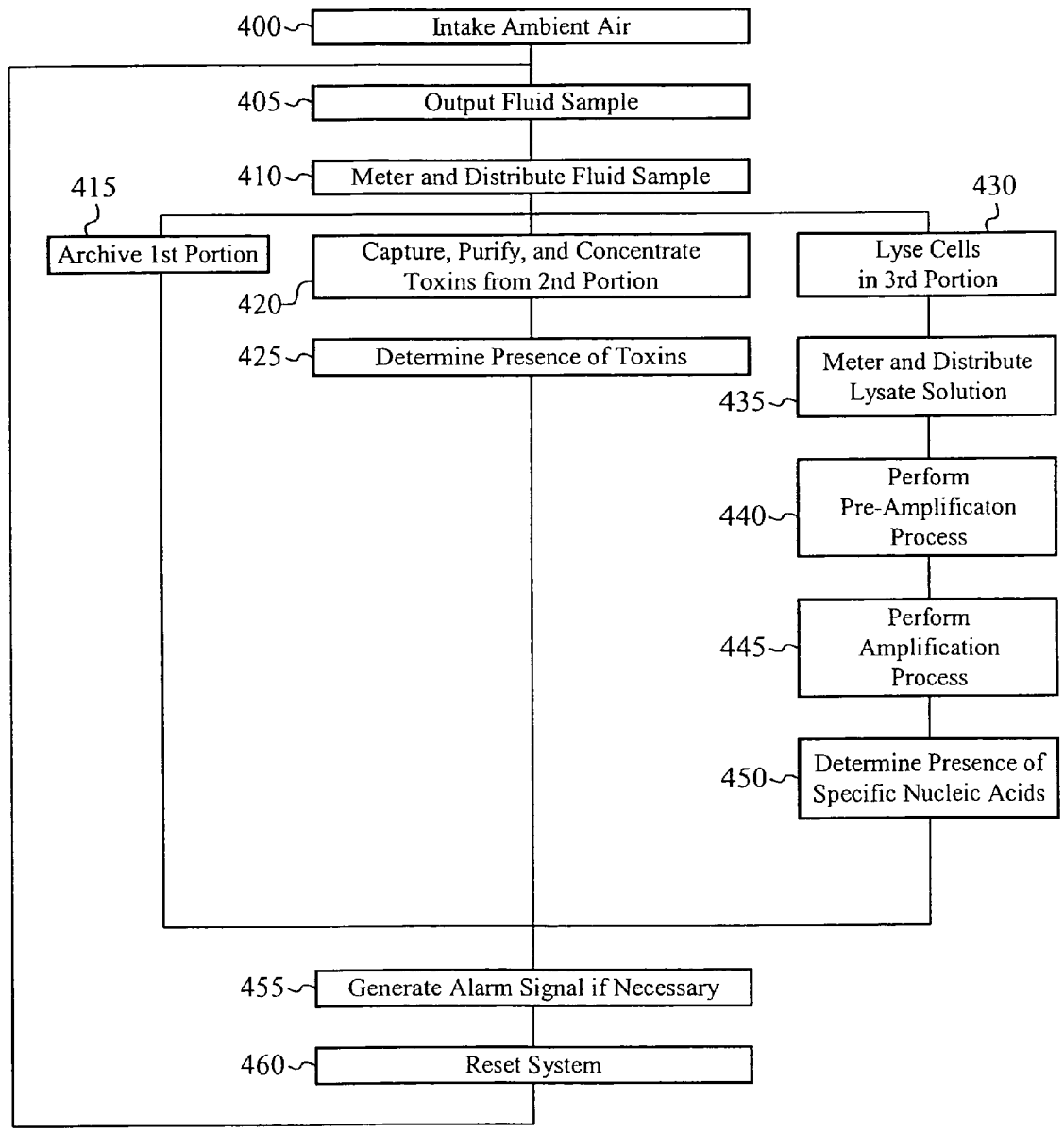
FIG. 9 illustrates an exemplary automated process performed by the first embodiment of the particle collection and detection system.

The particle collection and detection system 10 is a fully integrated and automated system configured to detect the presence of specific airborne particles. FIG. 9 illustrates an exemplary automated process performed by the particle collection and detection system 10. At the step 400, intake ambient air into the air collection module 14. Air is continuously taking in by the air collection module 14 throughout the entire process. At the step 405, periodically output a fluid sample from the air collection module 14 according to a defined schedule. The output fluid sample includes airborne particles collected from the ambient air. At the step 410, meter and distribute the fluid sample. At the step 415, archive a first portion of the fluid sample. At the step 420, capture, purify and concentrate toxins from within a second portion of the fluid sample. At the step 425, determine the presence of toxins captured in the step 420. In one embodiment, optical detection is used to detect the presence of toxins.

At the step 430, lyse cells in a third portion of the fluid sample. This generates a lysate solution. At the step 435, meter and distribute the lysate solution. At the step 440, perform a pre-amplification process on each metered portion of the first lysate. At the step 445, perform an amplification process on each metered portion of the first lysate to generate an amplified nucleic acid solution. The pre-amplification process and the amplification process include thermal cycling. At the step 450, determine the presence of one or more specific types of nucleic acids in the amplified nucleic acid solution and identifying the one or more specific types of nucleic acids. The steps 430 through 450 are performed in parallel with the steps 420 through 425, thereby simultaneously processing the fluid sample.

At the step 455, generate an alarm signal if one or more toxins are determined at the step 425 or one or more specific nucleic acids are determined at the step 450. At the step 460, reset the system to process the next fluid sample to be output by the air collection module 14. The system is reset by decontaminating the microfluidic circuitry through which the fluid sample passed, any fluid sample collection vessels, the capture devices used to capture the toxins, the purification devices used to purify the nucleic acids, any purged archive chambers, and the thermal cycling chambers. Decontamination is performed using any conventional rinsing and washing steps. After the system is reset, and at the next scheduled interval, the next fluid sample is output from the air collection module 14 and processed as described above. This process is continuously repeated for successive fluid samples. The particle collection and detection system functions independently, or is networked to a remote monitoring and/or control location to which measured characteristics and/or post-analysis results are transmitted and/or from which control signals are received.

In an exemplary application, the collection and detection system 10 operates continuously 24 hours a day, 7 days a week. Every three hours the air collection module outputs a 10 ml fluid sample to the distribution module 16. 1 ml of the 10 ml fluid sample is metered and distributed to the archive module 18, 3 ml to the toxin capture and detection module 22, and 6 ml to the lysis and capture module 20. The lysis and capture module 20 outputs a 50 ul sample for each 6 ml input sample. The metering and thermal cycling module 30 receives as input the 50 ul sample from the lysis and capture module 20 and 15 ul aliquots from the solutions module 32. The metering and thermal cycling module 30 outputs five, 25 ul samples for each 50 ul input sample received from the lysis and capture module 20. Each of the five, 25 ul samples are analyzed by the optical detection module 34. The above timing, sample sizes, and distribution ratios are for exemplary purposes only. The specific timing, sample sizes, and distribution ratios are application specific and the collection and detection system 10 is configured accordingly. Positive and negative control samples can be substituted for one or more of the 25 ul fluid samples processed by the metering and thermal cycling module 30, thereby verifying the accuracy of the analysis performed on any given input fluid sample.

A second embodiment of a collection and detection system is directed to a detect to warn system in which the presence of specific types of particles are detected, and may or may not be identified. FIG. 10 illustrates an exemplary functional block diagram of the second embodiment of the integrated collection and detection system. The integrated collection and detection system 500 includes an air collection module 510, a confirmation device 520, and a control module 530. Fluid is directed between the fluid interface 514 and the confirmation device 520, and within the confirmation device 520, using microfluidic circuitry.

The air collection module 510 is configured to intake ambient air, detect the presence of one or more different types of airborne particles within the ambient air, and collect the airborne particles, such as within a fluid. The air collection module 510 includes a triggering mechanism 512 and a fluid interface 514. The fluid interface 514 is configured to receive ambient air, including airborne particles present therein, that is drawn into the collection and detection system 500 and to collect the airborne particles into a fluid solution, also referred to as a fluid sample. The fluid interface 510 includes a fan to generate airflow into the collection and detection system 500. In some embodiments, the airborne particles are collected by eluting particles collected on the fan and then collecting the resulting fluid solution including the eluted particles. One such method of collecting the airborne particles into a fluid solution is described in the co-owned, co-pending U.S. patent application Ser. No. 11/509,878, filed Aug. 24, 2006, entitled "Automated Particle Collection Off of Fan Blades into a Liquid Buffer," which is hereby incorporated by reference. The fluid solution can be stored in a collection vessel within the fluid interface 514, or in a collection vessel external to the fluid interface 514 and/or the air collection module 510.

The triggering mechanism 512 is positioned to continuously monitor the airflow, and the airborne particles within the airflow, directed to the fluid interface 514. The triggering mechanism 512 includes a light source, such as a laser or a white-light LED, to generate a light beam that is directed at the airflow. The light beam impinges the airborne particles within the airflow. The triggering mechanism 512 also includes a light collector, such as an optical sensor, to measure one or more optical characteristics associated with the light after impinging the airborne particles. In some embodiments, the wavelength of the light reflected off the airborne particles is measured. The triggering mechanism 512 is non-destructive in relation to the airborne particles.

The optical characteristics measured by the triggering mechanism 512 are provided to the control module 530. The optical characteristics are compared to known optical characteristics by the control module 530 to determine if one or more different types of specific biological particles are present in the airflow. If it is determined that one or more different types of specific biological particles are present, than a trigger signal is generated by the control module 530. Alternatively, the triggering mechanism 512 includes logic circuitry to determine if one or more different types of specific biological particles are present and to generate the trigger signal, if necessary. Still alternatively, the triggering mechanism 512 includes logic circuitry to determine if one or more different types of specific biological particles are present, and the control module 530 generates the trigger signal, if necessary.

In response to the trigger signal, the fluid sample, or a portion thereof, is directed to the confirmation device 520 to confirm the presence of the one or more different types of specific biological particles. The confirmation device 520 includes a solutions module 522 and a toxin capture and detection module 524.

The toxin capture and detection module 524 of the second embodiment is physically and operationally equivalent to the toxin capture and detection module 22 of the first embodiment with the exception that the one or more capture devices and the optical detection module within the toxin capture and detection module 524 are configured to capture and detect specific pathogens in addition to specific toxins. Some pathogens are detectable using immuno assay. In some embodiments, the one or more capture devices within the toxin capture and detection module 524 are pre-coated with one or more specific antibodies known to adhere to specific pathogens, in addition to the one or more specific antibodies known to adhere to specific toxins as described in relation to the toxin capture and detection module 22. In these embodiments, the optical detection module within the toxin capture and detection module 524 is configured to measure one or more optical characteristics of any captured toxin or pathogen, which are used to determine the presence of each of the specific antibodies.

The raw data obtained by the toxin capture and detection module 524, such as the measured optical characteristics, is provided to the control module 530, where it is used to determine the presence and identity of one or more specific types of toxins and/or pathogens. If a specific toxin or pathogen is detected, the control module 530 generates an alarm signal. Alternatively, the raw data collected by the toxin capture and detection module 524 is sent to a remote location, such as the central monitoring point 50 (FIG. 1) for analysis.

The solutions module 522 is similar to the solutions module 26 (FIG. 2) in that it provides solutions used during the capture steps performed in the toxin capture and detection module 524. For example, the solutions module 522 includes wash solutions and antibody solutions.

The collection and detection system 500 is configured to be re-used such that ambient air is continuously interrogated and successive fluid samples output by the air collection module 510 are processed. As such, the toxins capture and detection module 524 and all interconnecting microfluidic circuitry are decontaminated between cycles. Various solutions are used to perform the rinse and wash steps during decontamination, these solutions are included in the solutions module 522.

The control module 530 is coupled to each module to control operation of the collection and detection system 500. Such control enables complete automation of the collection and detection process, without need of human intervention. The control module 530 is also configured to analyze the raw data provided by the toxin capture and detection module 524 and to generate any appropriate alarm or trigger signals. In response to an alarm signal, the control module 530 initiates a localized audio and/or visual alarm and/or transmits a notification signal to a networked local monitoring location or a centralized monitoring location.

The analyzed fluid samples, elution buffers, mixing solutions, rinses, washes, purged archive samples, and other solutions related to the processing of fluid samples and subsequent decontamination of the collection and detection system 500 are directed to a waste module (not shown). Alternatively, fluid samples analyzed and subsequently output by the toxin capture and detection module 524 can be archived, either in a local or a remote storage vessel.

FIG. 11 illustrates an exemplary automated process performed by the particle collection and detection system 500. At the step 540, intake ambient air into the air collection module 510. Air is continuously taken in by the air collection module 510 throughout the entire process. At the step 545, airborne particles within the ambient air are interrogated to measure one or more optical characteristics associated with the airborne particles. In some embodiments, a laser beam is used to interrogate the airborne particles such that the wavelengths of light reflected from the laser beam impinging the airborne particles is measured. At the step 550, the measured optical characteristics are compared to known optical characteristics associated with one or more different types of biological particles. If it is determined that there is not a match at the step 550, then the method repeats the step 540 and 545. If however it is determined that there is a match at the step 550, then at the step 555 a trigger signal is generated. Generation of the trigger signal indicates that at least one type of biological particle is present within the ambient air.

At the step 560, a fluid sample is generated that includes the particles from the ambient air. In response to the trigger signal, the fluid sample, or a portion thereof, is directed to the confirmation device 520. The step 560 can be performed after the step 545 such that the fluid sample is always generated, regardless of a match made between the measured optical characteristics and known optical characteristics. The step 560 can also be performed concurrently with the step 550, and if necessary the step 555. At the step 565, the confirmation device 520 confirms that one or more specific types of biological particles are present. The biological particles are either specific types of toxins or specific types of pathogens. In some embodiments, the confirmation device 520 confirms the presence of one or more different types of toxins and/or pathogens using immuno assays. In some embodiments, the confirmation device 520 identifies one or more of the different types of toxins and/or pathogens. In some embodiments, the confirmation device 520 generates an alarm signal if the presence of one or more different types of toxins and/or pathogens is confirmed.

Figure 10:
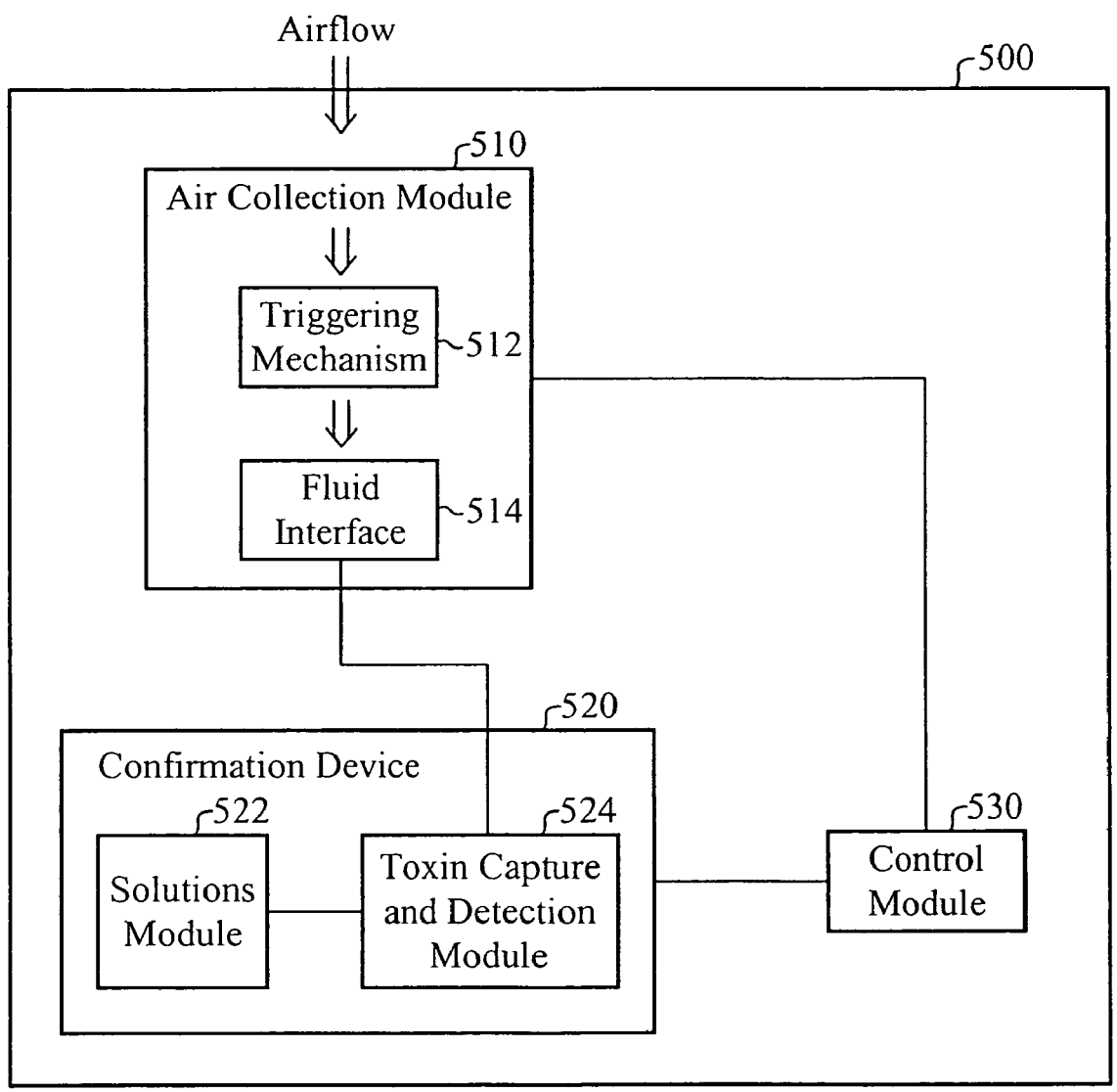
FIG. 10 illustrates an exemplary functional block diagram of the second embodiment of the integrated collection and detection system.

A third embodiment of a collection and detection system combines the functionality of the collection and detection system 10 of FIG. 1 and the collection and detection system 500 of FIG. 10. In this third embodiment, the collection and detection system 500 is adapted to perform a first level of detection in which the presence of one or more toxins and/or pathogens are detected, and upon such detection, the collection and detection system 10 is adapted to perform a second level of detection in which the one or more toxins and/or pathogens are identified.

Figure 12:
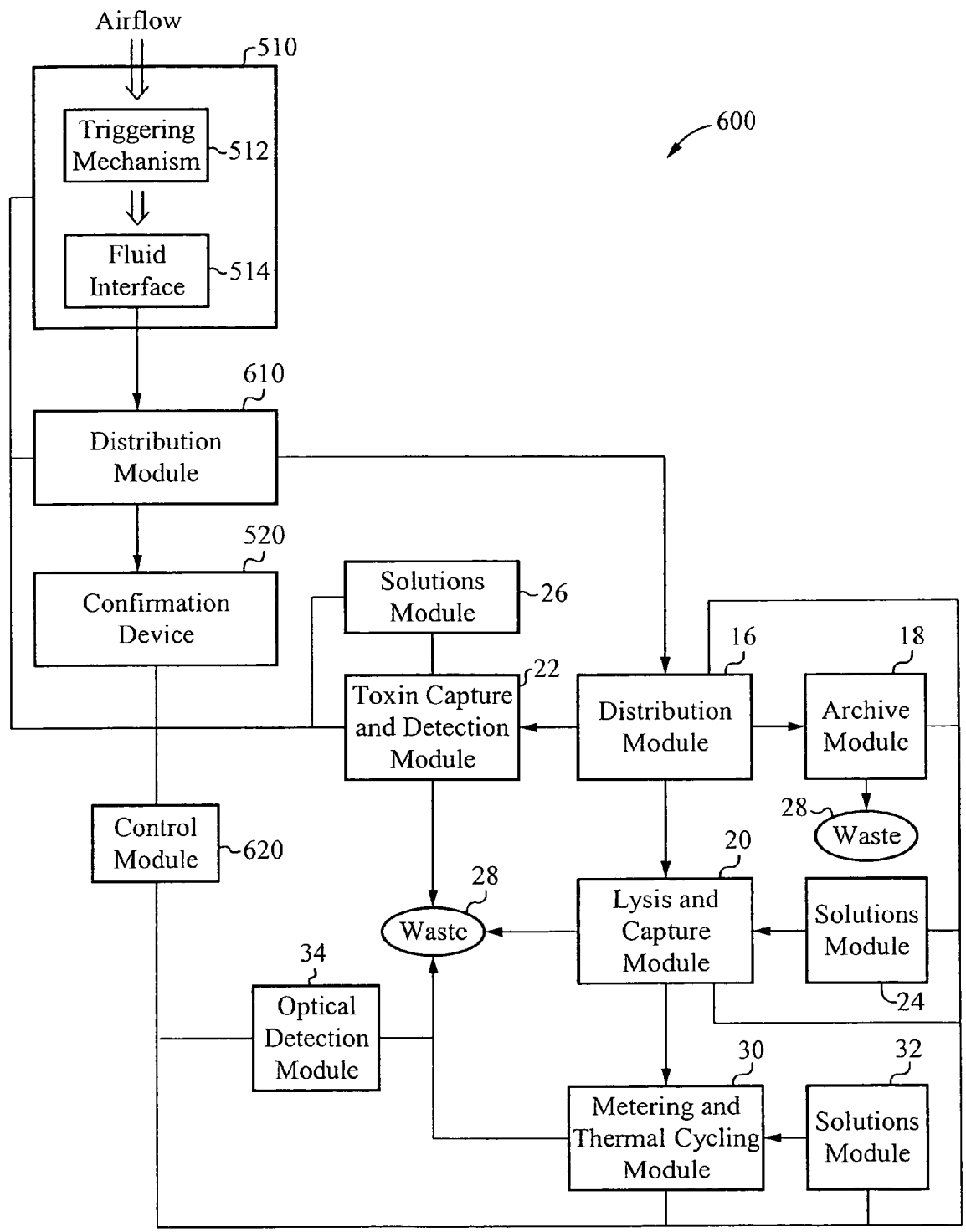
FIG. 12 illustrates an exemplary functional block diagram of the third embodiment of the integrated collection and detection system.

FIG. 12 illustrates an exemplary functional block diagram of the third embodiment of the integrated collection and detection system. The integrated collection and detection system 600 includes the air collection module 510 and the confirmation device 520 of the collection and detection system 500, and the distribution module 16, the archive module 18, the lysis and capture module 20, the toxin capture and detection module 22, the solutions module 24, the solutions module 26, the waste module 28, the metering and thermal cycling module 30, the solutions module 32, and the optical detection module 34 of the collection and detection system 10. The collection and detection system 600 also includes a distribution module 610 and a control module 620. Each of the modules are fluidically coupled as appropriate to direct fluid sample and solutions within the collection and detection system 600.

Control of the collection and detection system 600 is maintained by the control module 620, which includes the functionality of the control module 12 of the collection and detection system 10 and the control module 530 of the collection and detection system 500. Alternatively, control is distributed locally, such as by adding the control module 530 to control the first level of detection and by adding the control module 12 to control the second level of detection. Such local control modules communicate with each other to coordinate their respective functions. Still alternatively, control is distributed locally, such as by adding the control module 530 and the control module 12, and maintaining high-level control over the collection and detection system 600 by a global control module coupled to the local control modules. The control module 620 is coupled to each of the modules in the collection and detection system 600.

The distribution module 610 is configured to receive the fluid sample output from the fluid interface 514. The distribution module 610 includes microfluidic circuitry and storage vessels. The fluid sample received from the fluid interface 514 is metered and distributed according to predetermined ratios. A first portion of the fluid sample is metered and distributed to the confirmation device 520 in response to the trigger signal. The remaining portion of the fluid sample remains stored in the distribution module 610. If the confirmation device 520 confirms the presence of one or more specific types of biological particles, then the alarm signal is generated. In response to the alarm signal, the remaining portion of the fluid sample is distributed from the distribution module 610 to the distribution module 16. The fluid sample is then processed by the toxin capture and detection module 22, the lysis and capture module 20, the metering and thermal cycling module 20, and the optical detection module 34 to identify particles within the fluid sample. In some embodiments, a single distribution module can be configured to combine the functionality of the distribution module 610 and the distribution module 16.

If the triggering mechanism 512 does not generate a trigger signal, the fluid sample is stored in the distribution module 610 until the next scheduled interval for providing the fluid sample to the distribution module 16 to process. If the triggering mechanism 512 does generate a trigger signal but the confirmation device 520 does not generate an alarm signal, the remaining fluid sample is stored in the distribution module 610 until the next scheduled interval. Alternatively, if the triggering mechanism 512 does generate a trigger signal, the remaining fluid sample is distributed to the distribution module 16 to process whether or not the confirmation device 520 generates an alarm signal. The fluid interface 514 continues to output fluid sample to be stored in the distribution module 610 regardless of whether or not the trigger signal or alarm signal are generated.

In operation of the collection and detection system 600, the triggering mechanism 512 and the confirmation device 520 perform a first level of detection that determines if specific types of biological particles are present in the ambient air. If the first level of detection confirms the presence of one or more specific types of biological particles, a second level of detection is performed by the toxin capture and detection module 22, the lysis and capture module 20, the metering and thermal cycling module 20, and the optical detection module 34. The second level of detection identifies one or more specific toxins and/or one or more specific types pathogens.

FIG. 13 illustrates an exemplary automated process performed by the third embodiment of the particle collection and detection system. At the step 625, intake ambient air into the air collection module 510. Air is continuously taken in by the air collection module 510 throughout the entire process. At the step 630, airborne particles within the ambient air are interrogated to measure one or more optical characteristics associated with the airborne particles. In some embodiments, a laser beam is used to interrogate the airborne particles such that the wavelengths of light reflected from the laser beam impinging the airborne particles is measured. At the step 635, a fluid sample is generated that includes the particles from the ambient air. At the step 640, the measured optical characteristics are compared to known optical characteristics associated with one or more different types of biological particles. If it is determined that there is not a match at the step 640, then the method returns to the step 625. If however it is determined that there is a match at the step 640, then at the step 645 a trigger signal is generated. Generation of the trigger signal indicates that at least one type of biological particle is detected within the ambient air.

In response to the trigger signal, at the step 650 a first portion of the fluid sample is metered and distributed to the confirmation device 520. At the step 655, the confirmation device 520 confirms that one or more specific types of biological particles are present in the first portion of the fluid sample. The biological particles are either specific types of toxins or specific types of pathogens. In some embodiments, the confirmation device 520 confirms the presence of one or more different types of toxins and/or pathogens using immuno assays. In some embodiments, the confirmation device 520 identifies one or more of the different types of toxins and/or pathogens. If it is determined at the step 655 that the one or more specific types of biological particles are not present in the first portion of the fluid sample, then the method returns to the step 625. If however it is determined at the step 655 that the one or more specific types of biological particles are present in the first portion of the fluid sample, then at the step 660 a first alarm signal is generated. Generation of the first alarm signal indicates that at least one type of biological particle is detected within the first portion of the fluid sample.

At the step 665, a remaining portion of the fluid sample is metered and distributed to the archive module 18, the toxin capture and detection module 22, and the lysis and capture module 20. At the step 670, second portion of the fluid sample is archived. At the step 675, toxins from within a third portion of the fluid sample are captured, purified and concentrated. At the step 680, the presence of toxins captured in the step 675 is determined and the toxins are identified. In one embodiment, optical detection is used to detect and identify the toxins.

At the step 685, cells in a fourth portion of the fluid sample are lysed. This generates a lysate solution. At the step 690, the lysate solution is metered and distributed. At the step 695, a pre-amplification process is performed on each metered portion of the first lysate. At the step 700, an amplification process is performed on each metered portion of the first lysate to generate an amplified nucleic acid solution. The pre-amplification process and the amplification process include thermal cycling. At the step 705, the presence of one or more specific types of nucleic acids in the amplified nucleic acid solution is determined and the one or more specific types of nucleic acids are identified. The steps 685 through 705 are performed in parallel with the steps 675 through 680, thereby simultaneously processing the fluid sample.

At the step 710, a second alarm signal is generated if one or more toxins are determined at the step 680 or one or more specific nucleic acids are determined at the step 705. At the step 715, the system is reset in order to process the next fluid sample to be output by the air collection module 14. The system is reset by decontaminating the microfluidic circuitry through which the fluid sample passed, any fluid sample collection vessels, the capture devices used to capture the toxins, the purification devices used to purify the nucleic acids, any purged archive chambers, and the thermal cycling chambers. Decontamination is performed using any conventional rinsing and washing steps.

Embodiments of the integrated particle collection and detection system are described above in relation to a biothreat application. It is understood that the integrated particle collection and detection system can also be used to collect non-harmful air particles and in general the integrated particle collection and detection system can be used to collect and analyze any airborne particles.

The network configuration described in relation to FIG. 1 includes the first embodiment of the collection and detection system, the collection and detection system 10. It is understood that one, some, or all of the embodiments of the collection and detection system, for example the collection and detection system 10, the detection and collection system 500, and the collection and detection system 600, can be networked in a similar manner and in any combination.

The embodiments of the collection and detection system described above are for exemplary purposes. The microfluidic circuitry and module nature of the integrated collection and detection system provides flexibility and extensibility to interconnect and configure the modules, and associated sub-modular components, into any desired combination. Additionally, the specific configurations described for each of the modules is for exemplary purposes. The microfluidic circuitry and constituent components of each module can be adapted into any number of configurations to perform the described functionality.

The present invention has been described in terms of specific embodiments incorporating details to facilitate the understanding of the principles of construction and operation of the invention. The specific configurations shown and the methodologies described in relation to the air collection device, the confirmation device, the distribution module, the archive module, the lysis and capture module, the toxin capture and detection module, the metering and thermal cycling module, the optical detection module, the control module, and the interconnections therebetween are for exemplary purposes only. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A detection apparatus to detect the presence of one or more different types of particles, the detection apparatus comprises:
   a. a first level detection device configured to interrogate ambient air for the presence of one or more different types of airborne biological particles, wherein the first level detection device is further configured to generate a trigger signal in response to detecting one or more of the different types of airborne biological particles;
   b. a fluid interface configured to continuously receive airborne particles within the ambient air interrogated by the first level detection device and to continuously collect the particles within a fluid sample;
   c. a second level detection device configured to receive the fluid sample in response to the trigger signal and to confirm the presence of the one or more different types of biological particles using an immuno assay; and
   d. microfluidic circuitry to couple the fluid interface to the second level detection device.

2. The detection apparatus of claim 1 wherein the microfluidic circuitry includes a collection vessel to store the fluid sample.

3. The detection apparatus of claim 2 wherein the microfluidic circuitry is configured to meter the fluid sample into one or more portions and to distribute a first portion of the fluid sample to the second level detection device.

4. The detection apparatus of claim 1 wherein the second level detection device is configured to identify the one or more different types of biologic particles using the immuno assay.

5. The detection apparatus of claim 1 wherein the biologic particle comprises a pathogen.

6. The detection apparatus of claim 1 wherein the biological particle comprises a toxin.

7. The detection apparatus of claim 1 wherein the second level detection device comprises one or more capture devices each configured to capture one or more different types of biological particles from the fluid sample.

8. The detection apparatus of claim 7 wherein the second level detection device further comprises an optical detection module configured to optically detect the presence of the captured one or more different types of biological particles within the one or more capture devices.

9. The detection apparatus of claim 1 further comprising a control module configured to control the operation of the first level detection device, the fluid interface, and the second level detection device to enable the detection apparatus to function automatically.

10. The detection apparatus of claim 1 wherein the detection apparatus is configured to confirm the presence of the one or more different types of biological particles within about 5 minutes from generating the trigger signal.

11. The detection apparatus of claim 1 wherein the first level detection device comprises an air collection device configured to intake the ambient air to be interrogated.

12. The detection apparatus of claim 11 wherein the first level detection device further comprises a triggering mechanism configured to monitor the ambient air taken in by the air collection device and to generate the trigger signal.

13. The detection apparatus of claim 12 wherein the triggering mechanism comprises a light source configured to direct light onto the airborne particles and a light collector configured to measure one or more optical characteristics of light impinging the airborne particles.

14. An autonomously functioning detection apparatus to detect the presence of one or more different types of particles, the autonomously functioning detection apparatus comprises:

a. a first level detection device configured to automatically interrogate ambient air for the presence of one or more different types of airborne biological particles, wherein the first level detection device is further configured to automatically generate a trigger signal in response to detecting one or more of the different types of airborne biological particles;

b. a fluid interface configured to automatically and continuously receive airborne particles within the ambient air interrogated by the first level detection device and to automatically and continuously collect the particles within a fluid sample;

c. a second level detection device configured to automatically receive the fluid sample in response to the trigger signal and to automatically confirm the presence of the one or more different types of biological particles;

d. a control module configured to provide control signals to the first level detection device, the fluid interface, and the second level detection device to enable the detection apparatus to function autonomously; and e. microfluidic circuitry to couple the fluid interface to the second level detection device.

15. The autonomously functioning detection apparatus of claim 14 wherein the second level detection device is configured to automatically confirm the presence of the one or more different types of biological particles using an immuno assay.

16. The autonomously functioning detection apparatus of claim 15 wherein the second level detection device is configured to automatically identify the one or more different types of biologic particles using the immuno assay.

17. The autonomously functioning detection apparatus of claim 14 wherein the microfluidic circuitry includes a collection vessel to automatically store the fluid sample.

18. The autonomously functioning detection apparatus of claim 17 wherein the microfluidic circuitry is configured to automatically meter the fluid sample into one or more portions and to automatically distribute a first portion of the fluid sample to the second level detection device.

19. The autonomously functioning detection apparatus of claim 14 wherein the biologic particle comprises a pathogen.

20. The autonomously functioning detection apparatus of claim 14 wherein the biological particle comprises a toxin.

21. The autonomously functioning detection apparatus of claim 14 wherein the second level detection device comprises one or more purification devices each configured to automatically capture one or more different types of biological particles from the fluid sample.

22. The autonomously functioning detection apparatus of claim 21 wherein the second level detection device further comprises an optical detection module configured to optically detect the presence of the captured one or more different types of biological particles within the one or more purification devices.

23. The autonomously functioning detection apparatus of claim 14 wherein the autonomously functioning detection apparatus is configured to automatically confirm the presence of the one or more different types of biological particles within about 5 minutes from generating the trigger signal.

24. The autonomously functioning detection apparatus of claim 14 wherein the first level detection device comprises an air collection device configured to automatically intake the ambient air to be interrogated.

25. The autonomously functioning detection apparatus of claim 24 wherein the first level detection device further comprises a triggering mechanism configured to automatically monitor the ambient air taken in by the air collection device and to automatically generate the trigger signal.

26. The autonomously functioning detection apparatus of claim 25 wherein the triggering mechanism comprises a light source configured to automatically direct light onto the airborne particles and a light collector configured to automatically measure one or more optical characteristics of light impinging the airborne particles.

27. A detection apparatus to detect the presence of one or more different types of particles, the detection apparatus comprises:
   a. an air collection device configured to intake ambient air including airborne particles;
   b. a triggering mechanism configured to interrogate the ambient air for the presence of one or more different types of airborne biological particles and to generate a trigger signal in response to detecting one or more of the different types of airborne biological particles;
   c. a fluid interface configured to receive airborne particles within the ambient air interrogated by the triggering mechanism and to continuously collect the particles within a fluid sample;

d. a confirmation device configured to receive the fluid sample in response to the trigger signal and to confirm the presence of the one or more different types of biological particles using an immuno assay;

e. microfluidic circuitry to couple the fluid interface to the confirmation device; and f. a control module configured to provide control signals to the air collection device, the triggering mechanism, the fluid interface, and the confirmation device to enable the detection apparatus to function autonomously, wherein the air collection device, the triggering mechanism, the fluid interface, the confirmation device, and the control module are components of an integrated device.

28. The detection apparatus of claim 26 wherein the microfluidic circuitry includes a collection vessel to store the fluid sample.

29. The detection apparatus of claim 28 wherein the microfluidic circuitry is configured to meter the fluid sample into one or more portions and to distribute a first portion of the fluid sample to the confirmation device.

30. The detection apparatus of claim 27 wherein the confirmation device is configured to identify the one or more different types of biologic particles using the immuno assay.

31. The detection apparatus of claim 27 wherein the biologic particle comprises a pathogen.

32. The detection apparatus of claim 27 wherein the biological particle comprises a toxin.

33. The detection apparatus of claim 27 wherein the confirmation device comprises one or more purification devices each configured to capture one or more different types of biological particles from the fluid sample, further wherein each purification device includes an optically transparent portion configured to provide optical accessibility at a point of particle capture.

34. The detection apparatus of claim 33 wherein the confirmation device further comprises an optical detection module configured to optically detect the presence of the captured one or more different types of biological particles within the one or more purification devices.

35. The detection apparatus of claim 27 wherein the detection apparatus is configured to confirm the presence of the one or more different types of biological particles within about 5 minutes from generating the trigger signal.

36. The detection apparatus of claim 27 wherein the triggering mechanism comprises a light source configured to direct light onto the airborne particles and a light collector configured to measure one or more optical characteristics of light impinging the airborne particles.

37. A method of detecting the presence of one or more different types of biological particles, the method comprising:

a. continuously collecting ambient air including airborne particles;

b. measuring one or more optical characteristics of the airborne particles;

c. comparing the measured one or more optical characteristics to known optical characteristics associated with one or more types of biological particles;

d. continuously collecting the airborne particles measured for one or more optical characteristics within a fluid sample;

e. generating a trigger signal if the one or more of the measured one or more optical characteristics match one or more of the known optical characteristics; and f. in response to the trigger signal, transporting the fluid sample via microfluidic circuitry to a detection device and analyzing the fluid sample according to an immuno assay to confirm the presence of the one or more specific types of biological particles.

* * * * *

UNITED STATES PATENT AND TRADEMARK OFFICE
CERTIFICATE OF CORRECTION

PATENT NO. : 7,633,606 B2
APPLICATION NO. : 11/509872
DATED : December 15, 2009
INVENTOR(S) : Northup et al.

It is certified that error appears in the above-identified patent and that said Letters Patent is hereby corrected as shown below:

Column 23, line 59, please insert the word "continuously" between the words "to" and "receive" so that the limitation correctly reads:

-- c. a fluid interface configured to continuously receive airborne particles within the ambient air interrogated by the triggering mechanism and to continuously collect the particles within a fluid sample; --

Signed and Sealed this

Second Day of February, 2010

David J. Kappos

*Director of the United States Patent and Trademark Office*